US011634495B2

(12) United States Patent
Bürger et al.

(10) Patent No.: US 11,634,495 B2
(45) Date of Patent: Apr. 25, 2023

(54) METHODS OF ACTIVATING CD32B/C COMPRISING ADMINISTERING AN ANTIBODY THAT BINDS BDCA-2 (CD303)

(71) Applicant: Miltenyi Biotec B.V. & CO. KG, Bergisch Gladbach (DE)

(72) Inventors: Iris Bürger, Rösrath (DE); Martin Meyer, Kürten (DE); Andrzej Dzionek, Overath (DE)

(73) Assignee: Miltenyi Biotec B.V. & CO. KG, Bergisch Gladbach (DE)

( * ) Notice: Subject to any disclaimer, the term of this patent is extended or adjusted under 35 U.S.C. 154(b) by 237 days.

(21) Appl. No.: 16/603,519

(22) PCT Filed: Apr. 6, 2018

(86) PCT No.: PCT/EP2018/058857
§ 371 (c)(1),
(2) Date: Oct. 7, 2019

(87) PCT Pub. No.: WO2018/185284
PCT Pub. Date: Oct. 11, 2018

(65) Prior Publication Data
US 2020/0055941 A1 Feb. 20, 2020

(30) Foreign Application Priority Data
Apr. 7, 2017 (EP) .................................... 17165439

(51) Int. Cl.
*A61K 39/395* (2006.01)
*C07K 16/28* (2006.01)
*A61P 37/06* (2006.01)

(52) U.S. Cl.
CPC .......... *C07K 16/2851* (2013.01); *A61P 37/06* (2018.01); *C07K 2317/524* (2013.01); *C07K 2317/526* (2013.01); *C07K 2317/72* (2013.01); *C07K 2317/92* (2013.01)

(58) Field of Classification Search
None
See application file for complete search history.

(56) References Cited

U.S. PATENT DOCUMENTS

| 2004/0110226 A1* | 6/2004 | Lazar | C07K 16/32 435/7.1 |
|---|---|---|---|
| 2015/0017162 A1 | 1/2015 | Cummings et al. | |
| 2015/0299325 A1 | 10/2015 | Caravella | |

FOREIGN PATENT DOCUMENTS

| CN | 102482356 A | 5/2012 |
|---|---|---|
| CN | 104245729 A | 12/2014 |
| CN | 105452295 A | 3/2016 |
| EP | 1810979 B1 | 6/2012 |
| EP | 2928923 A1 | 10/2015 |
| EP | 3088519 A1 | 11/2016 |
| JP | 2002512776 A | 5/2002 |
| WO | 8807054 A1 | 9/1988 |
| WO | 1988007089 A1 | 9/1988 |
| WO | 1997034631 A1 | 9/1997 |
| WO | 1999051642 A1 | 10/1999 |
| WO | 1999058572 A1 | 11/1999 |
| WO | 2004035752 A2 | 4/2004 |
| WO | 2004092219 A2 | 10/2004 |
| WO | 2006/020114 A2 | 2/2006 |
| WO | 2006033386 A1 | 3/2006 |
| WO | 2008/145142 A1 | 5/2008 |
| WO | 2009/083009 A2 | 7/2009 |
| WO | 2010/105817 A2 | 9/2010 |
| WO | 2014/144542 A2 | 9/2014 |

OTHER PUBLICATIONS

Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14:2784-2794 (1995). (Year: 1995).*
D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018. 00395. (Year: 2018).*
Piche-Nicholas et al., Changes in complemetarity-determining regions significantly alter IgG binding to the neonatal Fc receptor (FcRN) and pharmacokinetics; MABS 2018, vol. 10, No. 1, 81-94, doi.org/ 10.1080/19420862.2017.1389355., (Year: 2018).*
Fanouriakis et al., Ann Rheum Dis 80: 14-25, 2021; doi: 10.1136/ annrheumdis-2020218272. (Year: 2021).*
Rendon et al., Int. J. Mol. Sci 2019 20, 1475; pp. 1-28. (Year: 2019).*
Nestle, et al. "Plasmacytoid predendritic cells initiate psoriasis through interferon-alpha production" The Journal of Experimental Medicine, Rockefeller University Press, US, vol. 202, No. 1, Jul. 4, 2005, pp. 135-143.

(Continued)

*Primary Examiner* — Phillip Gambel
(74) *Attorney, Agent, or Firm* — McDermott Will & Emery LLP

(57) ABSTRACT

The present invention relates to polypeptides comprising a mutant human IgG$_4$, which mutant human IgG$_4$ is capable of increasing the binding to and activation of immunoreceptor tyrosine-based inhibitory motif (ITIM)-containing FcγRIIb/c (CD32b), but not FcγRIIa (CD32a). More specifically, the invention relates to polypeptides comprising at least one human IgG$_4$ with a lysine at position 409 (409K), using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the prevention and/or treatment of an autoimmune disease or allergy, as further defined in the claims.

26 Claims, 8 Drawing Sheets
Specification includes a Sequence Listing.

(56) References Cited

OTHER PUBLICATIONS

Vidarsson, et al. "IgG Subclasses and Allotypes: From Structure to Effector Functions" Frontiers in Immunology, vol. 5, Oct. 20, 2014.
Chu, et al. "Inhibition of B cell receptor-mediated activation of primary human B cells by coengagement of CD19 and FCgammaRIIb with Fc-Engineered antibodies" Molecular Immunology, Pergamon, GB, vol. 45, No. 15, Sep. 1, 2008, pp. 3926-3933.
Aalberse, et al. "IgG4 breaking the rules." (Immunology 105 (2002); 9-19).
Bartholomaeus et al.: Cell contact-dependent priming and Fc interaction with CD32+ immune cells contribute to the TGN1412-triggered cytokine response. J Immunol 2014; 5: 2091-8.
Blank, et al.: Decreased transcription of the human FCGR2B gene mediated by the -343 G/C promoter polymorphism and association with systemic lupus erythematosus. Hum Genet 2005; 2-3: 220-7.
Blomberg et al.: Expression of the Markers BDCA-2 and BDCA-4 and Production of Interferon-alpha by Plasmacytoid Dendritic Cells in Systemic Lupus Erythematosus. Arthritis & Rheumatism 2003; 48(9): 2524-2532.
Bloom et al.: Intrachain disulfide bond in the core hinge region of human IgG4. (Protein Science vol. 6 (1997); 407-415).
Li, Xiaoli, Arthritis & Rheumatism, vol. 48, No. 11, 2003, 3242-3252.
Dzionek et al.: BDCA-2, BDCA-3, and BDCA-4: three markers for distinct subsets of dendritic cells in human peripheral blood. J Immunol. Dec. 1, 2000; 165(11): 6037-46.
Dzionek et al.: Plasmacytoid dendritic cells: from specific surface markers to specific cellular functions. Hum Immunol. Dec. 2002;63(12):1133-48.
Dzionek et al.: BDCA-2, a novel plasmacytoid dendritic cell-specific type II C-type lectin, mediates antigen capture and is a potent inhibitor of interferon alpha/beta induction. J Exp Med. Dec. 17, 2001; 194(12): 1823-34.
Forrer et al.: Chip-based gel electrophoresis method for the quantification of half-antibody species in IgG4 and their by- and degradation products. (Anal. Biochem. 334(1) (2004):81-88).
Horton et al. Antibody-Mediated Coengagement of FcγRIIb and B Cell Receptor Complex Suppresses Humoral Immunity in Systemic Lupus Erythematosus. J Immunol 2011; 186: 4223-4233.
Labrijn et al.: Therapeutic IgG4 antibodies engage in Fab-arm exchange with endogenous human IgG4 in vivo. (Nat Biotechnol. 27(8) (2009):767-71).
Means et al.: Human lupus atoantibody-DNA complexes activate DCs through cooperation of CD32 and TLR9. Journal of Clinical Investigation 2005; 115: 407-417.
Michelet et al.: Blood and Plasma Glutathione Measured in Healthy Subjects by HPLC: Relation to Sex, Aging, Biological Variables, and Life Habits. (Clinical Chemistry vol. 41, No. 10 (1995): 1509-17).
Mimoto et al.: Engineered antibody Fc variant with selectively enhanced FcγRIIb binding over both FcγRIIaR131 and FcγRIIaH131 . Protein Engineering, Design & Selection 2013; 26(10): 589-598.
Nevitt GJ. et al; Br J Dermatol. Oct. 1996, 135(4), 533-7.
Niewold, 2011. Interferon Alpha as a Primary Pathogenic Factor in Human Lupus. Journal of Interferon & Cytokine Research 31(12): 887-892.
Nimmerjahn, F. and J. V. Ravetch. 2008. Fcγ receptors as regulators of immune responses. Nature Reviews Immunology 1:34-47.
Rispens et al.: Human IgG4 binds to IgG4 and conformationally altered IgG1 via Fc-Fc interactions. J Immunol. 2009;182(7): 4275-4281.
Salfeld: Isotype selection in antibody engineering. (Nat. Biotechnol. ,vol. 25 No. 12 (2007):1369-72).
Schuurman et al.: The inter-heavy chain disulfide bonds of IgG4 are in equilibrium with intra-chain disulfide bonds. (Molecular Immunology 38(2001), 1-8).
Van Der Neut Kolfschoten: Anti-inflammatory activity of human IgG4 antibodies by dynamic Fab arm exchange. (Science. 317(5844) (2007):1554-7).
Veri et al.: Therapeutic control of B cell activation via recruitment of Fcgamma receptor IIb (CD32B) inhibitory function with a novel bispecific antibody scaffold. Arthritis Rheum. 2010; 62(7): 1933-1943.
Vidarsson et al.: IgG Subclasses and Allotypes: From Structure to Effector Functions. Frontiers in Immunology, vol. 5 (2014).
Vogel et al.: 2015. Antibody induced CD4 down-modulation of T cells is sitespecifically mediated by CD64(+) cells. Sci Rep 18308.
Christensen Sr et al, Semin Immunol. 2007, 19(1), 11-23, Epub Feb. 2, 2007. Review.
EMEA/UCHMP/SWSP/28367/07. Guideline on strategies to identify and mitigate risks for First-in-Human clinical trials with investigational medicinal products.
Wong SL et al., Clin Pharmacol Ther 2003 (73): 304.
Radstake Timothy et al, Arthritis & Rheumatism, vol. 54, No. 12, 2006, 3828-3837.
Catalán Diego, Arthritis Research & Therapy 2010, 12:R6.
Báve Ullvi, J Immunol. 2003, 171:3296-3302.
Su, kaihong, J Immunol 2007, 178:3272-3280.
Benitex-Ribas et al, "Plasmacytoid dendritic cells of melanoma patients present exogenous proteins . . . " JEM Brief definitve report, vol. 203, No. 7, 2006, 1629-1635.
Corrales-Aguillar E et al, J Immunol Methods, Jan. 31, 2013, 387(1-2): 21-35.
Jaehn Peter et al, BDCA-2 signaling inhibits TLR-9-agonist-induced plasmacytoid dendritic cell activation and antigen presentation, Cellular Immunology 2010.
Jaehn Peter et al., Eur. J. Immunol., 2008, 38: 1822-1832.
Swiecki Melissa et al, Eur. J. Immunol., 2007, 37: 3327-3329.
Zuckier Lionel S.et al, Cancer Research, 1998, 58: 3905-3908.
Bruhns Pierre, Blood 2012, 119: 5640-5649.
Ciccimarra F et al, Proc. Nat. Acad. Sci, USA, vol. 72, No. 6, 1975, 2081-2083.
Brusco A et al, "Molecular characterization of immunoglobulin G4 gene isoallotypes.", Eur J Immunogenet., (1998), vol. 25, No. 5, pp. 349 355.
Roeck Juergen et al, Eur. J. Immunol., 2007, 37: 3564-3575.
Vidarsson et al., IgG subclasses and allotypes: from structure to effector functions. Front Immunol. Oct. 20, 2014;5:520(1-17).

* cited by examiner

A

B

METHODS OF ACTIVATING CD32B/C COMPRISING ADMINISTERING AN ANTIBODY THAT BINDS BDCA-2 (CD303)

CROSS REFERENCE TO RELATED APPLICATION

The present application is a national stage filing under 35 U.S.C § 371 of International Patent Application No. PCT/EP2018/058857, filed Apr. 6, 2018, which claims the benefit of the European Patent Application No. 17165439.5 filed Apr. 7, 2017, the entire contents of each of which are incorporated herein by reference in their entireties.

INCORPORATION OF SEQUENCE LISTING

A computer readable text file, entitled "104882-70001US00-Sequence-Listing.txt" created on or about Oct. 7, 2019, with a file size of about 11 KB, contains the sequence listing for this application and is hereby incorporated by reference in its entirety.

The present invention relates to polypeptides comprising a mutant human $IgG_4$, which mutant human $IgG_4$ is capable of increasing the binding to and activation of immunoreceptor tyrosine-based inhibitory motif (ITIM)-containing FcγRIIb/c (CD32b), but not FcγRIIa (CD32a). More specifically, the invention relates to polypeptides comprising at least one human $IgG_4$ with a lysine at position 409 (409K), using the EU index according to Kabat et al., which $IgG_4$ is capable of binding to human CD32b/c with a statistically significant ($p=0.05$) higher binding affinity than a wild-type human $IgG_1$ and than a wild-type human $IgG_4$, for use in the prevention and/or treatment of an autoimmune disease or allergy, as further defined in the claims.

BACKGROUND OF THE INVENTION

For the proper selection of an antibody isotype, several points have to be considered for the later usage of the antibody as a therapeutic drug (Salfeld, 2007). All currently approved therapeutic antibodies are G-type immunoglobulins or derivatives of mouse, human or mixed origin. The four isotypes are characterized by different features (Table 1).

TABLE 1

Key features of the four IgG isotypes

| | IgG1 | IgG2 | IgG3 | IgG4 |
|---|---|---|---|---|
| Functional form in vivo | Monomeric bivalent | Dimeric tetravalent[a] | Monomeric bivalent | Half-Ig monovalent |
| Biological role in host response | Protein antigens | Carbohydrate antigens | Protein antigens | Response to chronic stimulation, anti-inflammatory |
| Percentage of all IgG in humans[b] | 60% | 25% | 10% | 5% |
| Half-life (range in days)[c] | 36.3 ± 9.2 (17.6-56.2) | 37.1 ± 13.9 (22.9-62.5) | 28.6 ± 10.4 (13.0-50.2) | 15.6 ± 4.5 (7.1-24.7) |
| Allotypes[d] | 4 | 1 | 13 | 0 |
| FcRn[e] | + | + | + | + |
| Hinge length (number of amino acids) | 15 | 12 | 62 | 12 |
| Potential (actual) inter-heavy chain disulfide bonds in hinge region | 2 (2) | 4 (4?[f]) | 11 (11) | 2 (2) |
| Effector functions | | | | |
| C1[e] | ++ | − | +++ | − |
| FcgRI[e] | +++ | − | +++ | ++ |
| FcgRII[e] | + | ± | + | ? |
| FcgRIIIa/b[e] | + | − | + | ± |

([a]Homodimers of $IgG_2$ are tetravalent for a given antigen, but heterodimers are also expected).

$IgG_3$ is characterized by a longer and more flexible hinge domain and the presence of 11 inter-heavy chain disulfide bridges (vs. 2 for $IgG_1$s and $IgG_4$s; 4 for $IgG_2$s). Despite a high antibody-dependent cellular cytotoxicity potential (ADCC), $IgG_3$ is generally not selected for therapeutic antibody development, probably due to a short half-life, susceptibility of the extended hinge region to proteolyses, and extensive allotypic polymorphism. $IgG_1$ is frequently selected for killing pathogenic cells (with an over-expressed target antigen) or viruses. To date, most of the current therapeutic chimeric, humanized and human antibodies are based on an $IgG_1$/kappa backbone.

$IgG_2$ and $IgG_4$ show specific structural and functional features like dynamic structural rearrangements, which are not observed for $IgG_1$. The advantage of the $IgG_4$-over the $IgG_1$-isotype is that $IgG_4$ does not mediate any effector functions, for example complement-mediated lysis (CML) and antibody-dependent cytotoxicity.

One of the disadvantages of $IgG_4$ is the formation of half-molecules. In vivo, $IgG_4$ antibodies are secreted as both, disulfide-linked tetramers and half-molecules, linked by strong non-covalent interactions. Non-covalently associated IgG$_4$ molecules dissociate into half-molecules on SDS-PAGE under non-reducing conditions. However, incubation with a reducing agent, e.g. dithiothreitol is needed (Bloom et al., 1997). In vitro and in vivo, half-molecules can bind the epitope, but blocks it without cross-linking. So, formation of half-molecules leads both to less functional antibodies and to a decreased therapeutic effect. In general, the formation of half-molecules is detected either by SDS-PAGE-analysis or chip-based gel electrophoresis in vitro (Forrer et al., 2004).

Moreover, IgG$_4$ can undergo Fab arm exchange. During Fab arm exchange, two IgG$_4$ tetramers associate and exchange one half-molecule, consisting of heavy and light chain resulting in bispecific antibodies (van der Neut Kolfschoten et al., 2007; Rispens et al., 2009). Fab arm exchange might be a problem in therapy with IgG$_4$ antibodies as they can undergo Fab arm exchange not only with each other but also with endogenous IgG$_4$. The mechanism by which IgG$_4$ Fab arm exchange occurs in vivo demands the reducing environment of blood, caused by 0.8±0.2 mM GSH (Michelet et al., 1995), or cell surfaces to facilitate the breaking of the inter-heavy chain disulfide bond within the hinge-region (van der Neut Kolfschoten et al., 2007). For example, natalizumab (marketed under the trademark Tysabri®), a clinical non-stabilized IgG$_4$, undergoes Fab arm exchange in vitro and in vivo (Labrijn et al., 2009). Fab arm exchange can lead to bispecific and monovalent antibodies. So, cross-linking is no longer possible. Due to the above disadvantages, IgG$_4$ isotype is usually not the first choice in the development of therapeutic antibodies.

It was shown that mutation of Ser228 to Pro stabilizes IgG$_4$, as an intrachain-disulfide bond cannot be formed easily (Schuurman et al., 2001). For example, Mylotarg is a therapeutic IgG$_4$-antibody with S228P-mutation that blocks Fab arm exchange both in vitro and in a mouse model (Labrijn et al., 2009).

Moreover, current literature data show that amino acid differences in the CH3 domain of the IgG$_4$ Fc-part as compared to the IgG$_1$ Fc-part are critical for Fab arm exchange in addition to the IgG$_4$ hinge-region (van der Neut Kolfschoten et al., 2007). The IgG$_1$ and IgG$_4$ CH3 domains differ in five amino acid residues, of which only one amino acid is within the CH3 inter-domain interface. This amino acid is located on position 409 and it is lysine (K409) and arginine (R409) within the IgG$_1$ and IgG$_4$ isotype, respectively. Therefore, K409 seems to play a significant role in preventing IgG$_1$ molecules from building half-molecules.

Approaches for immunosuppression via increasing binding to CD32b or its cross-linking have been patented and described, e.g. an receptor-attracting monoclonal antibody (WO 2009/083009), bispecific monoclonal antibodies (e.g. anti-CD79B/anti-CD32B by Veri et al., 2010) and "bifunctional" monoclonal antibodies (e.g. anti-CD19 and modified Fc region of IgG$_1$-S267E/L328F by Xencor, Horton et al (2012) and PMID:22257644 with increased affinity for both CD32a and CD32b). Another modified Fc region of an IgG$_1$ was described by Mimoto et al. (2013) using IgG$_1$-P238D/L328E, enhancing only CD32b affinity.

WO 2014/144542 A2 discloses bioactive peptide amino acid sequences which inhibit the complement system, and further discloses that such bioactive peptide amino acid sequences may be fused to a human IgG$_4$. The thus modified antibody may be used in the treatment of psoriasis.

Vidarsson et al.: IgG Subclasses and Allotypes: From Structure to Effector Functions. Frontiers in Immunology, Vol. 5 (2014), confirm that both IgG$_4$ and IgG$_1$ have binding affinity to the inhibiting Fc receptor CD32b.

Chu et al. Molecular Immunology 45(15): 3926-3933 (2008) suggest that IgG$_1$-Fc has a high binding affinity to CD32b, and may have broad applicability in various atoimmune diseases.

The object of the present disclosure is to provide therapeutic IgG$_4$ molecules with improved properties such as an increased binding to and activation of the inhibitory Fc receptor CD32b/c. In the context of the prevention and/or treatment of an autoimmune disease or allergy, the therapeutic IgG$_4$ molecules of the invention are expected to result in an improved therapeutic effect, if administered on a regular basis.

SUMMARY OF THE INVENTION

Surprisingly, it was found that point mutation R409K in the constant region of IgG$_4$ increased the affinity of the IgG$_4$ antibody for CD32a and CD32b/c, both are FcγRIIa/b receptors. As typical IgG$_4$ molecule it was expected that it does not show any affinity or functional interactions with human Fcγ receptors like CD16a, CD32a, CD32b/c and CD64. Further, upon functional analysis, it could be shown that only CD32b/c can be activated by such an antibody. Different wild-type human IgG$_1$ and IgG$_4$ antibodies, which were used as controls, showed significantly lower affinity for CD32b/c.

CD32b/c contains an immunoreceptor tyrosine-based inhibitory motif (ITIM) within its intracellular domain and acts as a inhibitory receptor (PMID:14613290). CD32b/c is mainly present on B cells, but also on CD14$^+$ monocytes and myeloid dendritic cells (mDCs) & plasmacytoid dendritic cells (pDCs) and plays an important role in the maintenance of tolerance (PMID:17312177). As triggering of CD32b/c dependent inhibitory signaling pathway in activated B cells leads to the inhibition of B cell proliferation and Ig secretion (PMID: 20506263), stabilized human IgG$_4$ as described above could therefore be useful as therapeutic agent in inflammatory or auto-antibody mediated autoimmune diseases like e.g. SLE, psoriasis, multiple sclerosis and rheumatoid arthritis; or in allergy.

The mutant human IgG$_4$ mAb with its high affinity and activation potential for the CD32b/c receptor, when used for therapeutic purpose, may induce the CD32b/c dependent signaling in vivo either after being immobilized on the cell surface of other immune and endothelial cells (dependent on its specificity) or after being complexed by specific (anti-drug) antibodies, which are occasionally developed upon antibody administration during antibody based therapies. In addition, antibodies consisting of the mutant human IgG$_4$ backbone with specificity for cell surface receptors, which are expressed on cells expressing CD32b/c, could be used to specifically inhibit their activation. Such antibodies could bind to the given cell specific receptor (e.g. CD304, CD303, ILT7, CD123 on PDCs or CD19, CD20, BCR on B cells or CD14, CD11c on monocytes) and at the same time bind and cross-link the CD32b/c on the cell surface of the very same cell or on the cell surface of the second cell, which interact with the cell, where the antibody has originally bound.

Accordingly, the above-stated object is deemed to be solved by a polypeptide comprising at least one human IgG$_4$ with a lysine at position 409 (409K), using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of an autoimmune disease in a human subject, as further defined in the claims. Likewise, the foregoing object is also deemed to be solved by provision of a polypeptide comprising at least one human IgG$_4$ with a lysine at position 409 (409K), using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of allergy in a human subject, as further defined in the claims.

DETAILED DESCRIPTION OF THE PREFERRED EMBODIMENTS

Fcγ receptors (FcγR), which are widely expressed amongst cells of the hematopoietic system, bind the Fc part of IgG antibodies. In the human system the family of FcγR is divided into three main classes, FcγRI (CD64), FcγRII (CD32) and FcγRIII (CD16), each one showing distinct structural and functional properties. In humans each group of receptors is encoded by 2-3 closely related genes designated A, B, and C. Binding of immune complexes to activating FcγR, i.e., CD16, CD32A, and CD64, induces a phosphorylation cascade that leads to cell activation characterized by calcium flux and cytokine release. On the contrary, triggering of the inhibitory FcγR (CD32b/c) expressed by B cells induces apoptosis. In contrast, concomitant stimulation of CD32b/c together with an activating receptor (such as the B cell receptor) leads to inhibition of calcium flux and proliferation, i.e., blocking of cell activation (Nimmerjahn and Ravetch, 2008). CD32b/c is expressed on B cells and on a variety of other cell types such as macrophages, neutrophils, and DC. CD32b/c as the only inhibitory receptor comprising an ITIM domain in the intracellular part of the receptor is known to be important in several regulatory processes. Recent data indicated that impairment of CD32b/c signaling is associated with autoimmune disorders such as SLE (Blank et al., 2005).

With the development of many different new monoclonal antibodies (mAb) as therapeutics, FcγR interactions came back into the research focus. Several mAb effector functions such as phagocytosis, induction of inflammatory cytokines or chemokine release and antibody-dependent cytotoxicity (ADCC) are mediated by the interaction of the Fc part with FcγR expressing immune cells, thus shaping the therapeutic potential of mAbs. For example, in a recent study FcγR interactions boosted T cell activation upon treatment with a superagonistic anti-CD28 mAb (Bartholomaeus et al., 2014), whereas in another study with an agonistic anti-CD4 mAb FcγR interactions were needed to induce CDD4 downmodulation of mAb decorated T cells (Vogel et al., 2015).

The present inventors surprisingly found that binding of human IgG$_4$ to and activation of the human CD32b/c Fcγ receptor can be increased by introducing a mutation into the constant region of the IgG$_4$. More specifically, the present disclosure provides a polypeptide comprising at least one human IgG$_4$ with a lysine at position 409 (409K), using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of an autoimmune disease in a human subject, as further defined in the claims.

Examples of an autoimmune disease are Addison's disease, agammaglobulinemia alopecia areata, amyloidosis, ankylosing spondylitis, anti-GBM/anti-TBM nephritis, antiphospholipid syndrome (APS), autoimmune hepatitis, autoimmune inner ear disease (AIED), axonal & neuronal neuropathy (AMAN), Behcet's disease, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid/benign mucosal pemphigoid, Cogan's syndrome, cold agglutinin disease, congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, Fibrosing alveolitis, giant cell arteritis (temporal arteritis), giant cell myocarditis, glomerulonephritis, Goodpasture's syndrome, granulomatosis with polyangiitis, graves' disease, Guillain-Barre syndrome, Hashimoto's thyroiditis, hemolytic anemia, Henoch-Schonlein purpura (HSP), Herpes gestationis or pemphigoid gestationis (PG), hypogammalglobulinemia, IgA nephropathy, 1 gal-related sclerosing disease, Inclusion body myositis (IBM), Interstitial cystitis (IC), juvenile arthritis, juvenile diabetes (Type 1 diabetes), juvenile myositis (JM), Kawasaki disease, Lambert-Eaton syndrome, leukocytoclastic vasculitis, Lichen planus, Lichen sclerosus, ligneous conjunctivitis, linear IgA disease (LAD), lupus, lyme disease chronic, Meniere's disease', microscopic polyangiitis (MPA), mixed connective tissue disease (MCTD), Mooren's ulcer, Mucha-Habermann disease, multiple sclerosis (MS), myasthenia gravis, myositis, narcolepsy, neuromyelitis optica, neutropenia, ocular cicatricial pemphigoid, optic neuritis, palindromic rheumatism (PR), PANDAS (Pediatric Autoimmune Neuropsychiatric Disorders Associated with *Streptococcus*), paraneoplastic cerebellar degeneration (PCD), paroxysmal nocturnal hemoglobinuria (PNH), Parry Romberg syndrome, Pars planitis (peripheral uveitis), Parsonnage-Turner syndrome, pemphigus, peripheral neuropathy, perivenous encephalomyelitis, pernicious anemia (PA), POEMS syndrome, (polyneuropathy, organomegaly, endocrinopathy, monoclonal gammopathy, skin changes), Polyarteritis nodosa, polymyalgia rheumatic, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, Reiter's syndrome, relapsing polychondritis, restless legs syndrome (RLS), retroperitoneal fibrosis, rheumatic fever, rheumatoid arthritis (RA), sarcoidosis, Schmidt syndrome, scleritis, scleroderma, Sjogren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/Giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, and Wegener's granulomatosis (now termed Granulomatosis with Polyangiitis (GPA). Moreover, particularly contemplated patient groups are those human subjects, which show a dysregulation of CD32b expression, as compared to healthy subjects. For example, the human subject may exhibit a CD32b 695T allele and/or a 2B.4 haplotype of the CD32b gene. Alternatively, the human subject may have a CD32b 695C allele and/or a 2B.1 haplotype of the CD32b gene.

Activation of CD32b/c on immune cells such as B cells, PDC or monocytes is believed to result in a down-modulation of these cells. Therefore, it is contemplated that the polypeptide comprising at least one human IgG$_4$ with a lysine at position 409 (409K) can be advantageously used in the prevention or treatment of an inflammatory autoimmune disease. The autoimmune disease may be further characterized by increased plasma levels of autoantibodies as compared to healthy subjects. In further embodiments, the autoimmune disease may be characterized by an increased type I interferon production, such as increased interferon-alpha production, as compared to healthy subjects.

In a preferred embodiment, the autoimmune disease is selected from the group consisting of psoriasis, systemic lupus erythematosus, rheumatoid arthritis, and multiple sclerosis; and in a more preferred embodiment the autoimmune disease is systemic lupus erythematosus or psoriasis.

Autoantibody immune complexes activate various immune cells such as dendritic cells and B cells via binding to the activating Fc receptor CD32a and subsequent internalization and activation of pattern recognition receptors, e.g. Toll Like Receptors. This, in turn, leads to increased production of pro-inflammatory cytokines such as type-I interferon, in particular of interferon alpha, which again triggers the production of autoantibodies. As shown in the examples below, the IgG$_4$ variants disclosed herein do not only bind to the inhibitory Fc receptor CD32b/c with high (or higher) affinity as compared to wild-type IgG$_4$, as probably also other immunoglobulines. As shown in the examples, mere binding of an immunoglobuline to CD32b/c does not automatically result in (improved) activation. Rather, the examples herein show that the IgG$_4$ variants disclosed herein are particularly suitable for activating the inhibitory Fc receptor CD32b/c, thereby inhibiting the activation of dendritic cells and B cells via CD32a. As further demonstrated in the examples below, in particular the embodiments wherein the polypeptide comprises an IgG$_4$ which recognizes an epitope of BDCA-2 (CD303) are particularly advantageous in the treatment of the above-mentioned diseases. This is because targeting BDCA-2 was demonstrated to inhibit type-I interferon production, in particular interferon-alpha production. Accordingly, it is plausibly demonstrated that the polypeptides of the present disclosure can be advantageously applied in a new therapeutic application, which involves the activation of CD32b/c on CD32b/c expressing cells in the prevention and/or treatment of an autoimmune disease in a human subject, in particular wherein the polypeptide comprises an IgG$_4$ which recognizes an epitope of BDCA-2 (CD303). As discussed in the examples, psoriasis is an autoimmune disease in which interferon alpha and autoantibodies play a key role in pathogenesis. The same holds true for the other autoimmune diseases recited above. For example, it was generally known that interferon alpha is a primary pathogenic factor in human systemic lupus erythematosus, as reviewed in Niewold, Journal of Interferon & Cytokine Research 31(12), 887-892 (2011). As shown in FIG. 1 on page 889 therein, Autoantibody immune complexes binding to and internalized by Fc receptors play a pivotal role in pathogenesis.

This pivotal role was demonstrated by Means et al., J Clin Invest. 115(2), 407-417 (2005): Correlation between disease severity and IFN-alpha levels in SLE patients and mitigation of disease in a mouse model of SLE by disruption of IFN-alpha signaling have implicated IFN-alpha in SLE pathogenesis. High levels of IFN-alpha in the serum of SLE patients have been postulated to play a role in the loss of tolerance to autoantigens in SLE. It has been demonstrated that IFN-alpha in the serum of SLE patients drives the maturation of monocytes into dendritic cells. The ability of these mDCs to engulf apoptotic cells and activate autoreactive T cells and B cells has been hypothesized to drive the autoimmune response in SLE. It was finally demonstrated that stimulation of PDCs with DNA-containing immune complexes from SLE patients through the TLR9/CD32 pathway induced robust expression of IFN-alpha by PDC.

Notably, it could also be demonstrated that anti-BDCA-2 antibodies are capable of inhibiting IFN-alpha production in SLE patients (Blomberg et al. Arthritis & Rheumatism, 48(9), 2524-2532 (2003); Dzionek et al. J Exp. Med. 194 (12), 1823-1834 (2001)), and that reduction of interferon-alpha activity in SLE patients has therapeutic benefit (cf. clinical trial NCT00299819 for sifalimumab, an anti-IFN-alpha monoclonal antibody). Accordingly, the therapeutic suitability of the polypeptide of the present disclosure is not only demonstrated by the experimental data shown herein below, but also in light of the known effects and the known pathogenesis in SLE.

In light of the facts and evidence provided herein with regard to psoriasis and SLE, the present inventors are of the opinion that the effects and therapeutic benefits demonstrated herein can be extrapolated to any of the above-mentioned diseases, in particular the autoimmune diseases characterized by increased plasma levels of autoantibodies as compared to healthy subjects and/or by an increased type I interferon production, such as increased interferon-alpha production, as compared to healthy subjects, such as rheumatoid arthritis and multiple sclerosis, or any other of the above-disclosed autoimmune diseases. Similar considerations apply to allergies, which are characterized by high IgE titers, resulting in IgE-antigen immune complexes which may in turn activate CD32 bearing B cells or monocytes.

The polypeptide may be any polypeptide as long as it comprises at least one human IgG$_4$ constant region comprising the R409K substitution. For example, the polypeptide may be a fusion protein which is able to bind to CD32b/c, and which contains the mutant IgG$_4$ constant region of the present disclosure. For example, the mutant human IgG$_4$ disclosed herein is fused to a ligand molecule or a soluble receptor molecule. Alternatively, the polypeptide may comprise two Fc regions, e.g. two human IgG$_4$ Fc regions (e.g. fused tail-to-tail), or one human IgG$_4$ Fc region fused to a human IgG$_1$ Fc region.

However, as demonstrated herein, the (therapeutic) effects are obtained by the herein disclosed polypeptide as such, and not dependent on a fusion to a bioactive peptide amino acid sequences as, e.g. described in WO 2014/144542 A2. In the latter, the pharmaceutical effects are disclosed in the context of particular peptide sequences which are fused to, for example, IgG$_4$. Accordingly, in a preferred embodiment, the polypeptide is not fused to a bioactive peptide amino acid sequence which acts as the pharmaceutically active agent.

Also contemplated within the polypeptide of the present disclosure are monomeric antibodies bearing the mutant IgG$_4$ constant region of the present disclosure, e.g. chimeras in which the human IgG$_4$ constant region is fused to a variable region of an antibody of another isotype or species.

In a particularly preferred embodiment, the human IgG$_4$ comprises a further substitution, e.g. a substitution which is known to further stabilize the human IgG$_4$ molecule. Such substitutions are known in the field. Particularly contemplated is an embodiment, wherein the human IgG$_4$ further comprises a proline at position 241 (241 P), using the EU index according to Kabat et al. In another embodiment, the human IgG$_4$ further comprises a proline at position 228 (228P), using the EU index according to Kabat et al. In still another embodiment, the human IgG$_4$ further comprises a proline at position 228 (228P) and a proline at position 241 (241P), using the EU index according to Kabat et al.

In certain embodiments, the mutant IgG$_4$ constant region of the present disclosure has a sequence identity of at least 95% over the whole length of SEQ ID NO: 1, more preferably a sequence identity of at least 96% over the whole length of SEQ ID NO: 1, more preferably a sequence identity of at least 97% over the whole length of SEQ ID NO: 1, more preferably a sequence identity of at least 98% over the whole length of SEQ ID NO: 1, and most preferably a sequence identity of at least 99% over the whole length of SEQ ID NO: 1.

In a special embodiment, the human IgG$_4$ comprises the amino acid sequence of SEQ ID NO: 1 (hIgG4) with a lysine at the position corresponding to position 409 (409K) and a proline at the position corresponding to position 241 (241 P), using the EU index according to Kabat et al.

Generally, an amino acid sequence has "at least x % identity" with SEQ ID NO: 1, when the sequence identity between the aligned sequences is at least x % over the full length of SEQ ID NO: 1. Such an alignment can be performed using publicly available computer homology programs, e.g., the "BLAST" program provided at the NCBI homepage at http://www.ncbi.nlm.nih.gov/blast/blast.cgi, using the default settings provided therein.

The human IgG$_4$ Fc bearing the R409K substitution is capable of binding to human CD32b/c with a statistically significant (p=0.05) higher binding affinity than a wild-type human IgG$_1$ and than a wild-type human IgG$_4$. The expression "binding to human CD32b/c with a statistically significant (p=0.05) higher binding affinity than a wild-type human IgG$_1$ and than a wild-type human IgG$_4$" as used herein means that the polypeptide comprising the at least one human IgG$_4$ Fc bearing the R409K substitution shows a statistically significant (p=0.05) higher binding affinity as compared to a non-relevant wild-type human IgG$_4$ and a wild type human IgG$_1$ (or a polypeptide comprising said wild-type human IgG$_4$ and a wild type human IgG$_1$ instead of the human IgG$_4$ bearing the R409K mutation), when subjecting the polypeptide and the wild type antibodies to the following assay:

ELISA plates are coated with recombinant Fcγ receptor IIb (e.g., R&D Systems, 1875-CD-050) with 5 µg/mL in coating buffer overnight at 4° C. Coated plates are washed 3-fold with 1×PBS 0.05% Tween 20 and blocked with 5% BSA in 1×PBS. The polypeptide and antibodies are applied to ELISA plates with 50 µL/well (or at the same molar concentration corresponding to 50 µg human IgG$_4$ per well) at serial 2-fold dilution of antibody solution and incubated at room temperature for 1 h. As blank controls, respective antibody concentrations are also applied to wells lacking coated Fcγ receptors, in order to subtract unspecific binding from resulting signals. After washing (see above), the detection antibody (e.g., anti-human kappa-HRP, FE 110316.07, at 1:4000; or another commercially available anti-IgG$_4$-HRP conjugated antibody or anti-IgG$_1$-HRP conjugated antibody applied in a dilution in accordance with the manufacturers instruction) in 1×PBS is applied with 50 µL/well and incubated again at RT for 1 h. After additional washing as described above, for assay development 50 µL/well TMB (CH111027.37) are applied and stopped after approx. 5 minutes with 50 µL/well 10% H$_2$SO$_4$. The developed plate is then analyzed via ELISA reader at 450 nm wavelength. In order to further improve the comparability, one may also prepare a standard curve applying different known amounts of IgG$_4$ and/or IgG$_1$ which are then correlated to the absorbance at 450 nm wavelength.

Alternatively, the human IgG$_4$ with a lysine at position 409 (409K using the EU index according to Kabat et al.) described herein is capable of binding to human CD32b/c with a higher binding affinity of at least 2-fold, preferably at least 5-fold and most preferably at least 10-fold than the binding affinity of a wild-type human IgG$_1$ and/or a wild-type human IgG$_4$, as determined by using the above assay. As shown in the examples, the human IgG$_4$ 409K shows an increased activation of human CD32b/c as compared to wt human IgG$_4$ and/or wt human IgG$_1$. The expression "increased activation of human CD32b/c as compared to wt human IgG$_4$ and/or wt human IgG$_1$" as used herein is intended to mean that the polypeptide of the invention activates CD32b/c stronger than a wild type human IgG$_4$ and/or wild type human IgG$_1$ (or a corresponding polypeptide comprising a wild type human IgG$_4$ and/or wild type human IgG$_1$ instead of the human IgG$_4$ 409K). This feature can be tested by using the following activation assay. As apparent from this definition, binding to CD32b/c does not automatically result in an increased activation of human CD32b/c. Indeed, the surprising aspect of the present invention is that the polypeptide of the present disclosure triggers increased activation of CD32b/c upon binding to the receptor.

To test the ability of different mAbs to bind to and to cross-link the individual FcγRs, mAbs are coated to plastics and a murine thymoma cell line BW5147 transfected with a fusion protein consisting of the extracellular domain of CD32b and the transmembrane and intracellular ζ-chain of the murine T cell receptor is added. If a mAb interacts with a tested FcγR, murine IL-2 production is induced. Absolute IL-2 levels are taken as readout of Fcγ-CD32b/c-interaction. Tests with control mAbs of the wild type IgG$_4$ and/or IgG$_1$ (or a corresponding polypeptide comprising a wild type human IgG$_4$ and/or wild type human IgG$_1$ instead of the human IgG$_4$ 409K) allow comparative evaluation of interaction strength. This experimental setting is suited to study conditions of Fc-FcR-interactions that are also relevant in vivo, when a mAb is bound to a cell-surface target and interacts with Fc-receptors on different immune cells. The production of the reporter cell line is further described in Example 2 below.

The polypeptide of the disclosure, wild type human IgG$_4$, wild type human IgG$_1$, or a corresponding control polypeptide comprising a wild type human IgG$_4$ and/or wild type human IgG$_1$ instead of the human IgG$_4$ 409K, are serially 3-fold diluted in 1:10 (total log 3 dilution) in binding buffer (10 mM Bis-Tris, pH 6) starting with a concentration of 10 µg/ml. 100 µl of each dilution is transferred to a single well and the coating is performed over night at 4° C. After removal of the coating reagent, 200 µl per well blocking buffer (PBS+FCS 10%) are added and incubated for 1 h at RT. After blocking, the wells are washed 3 times with 300 µl PBS. CD32b-expressing BW5147 reporter cells are transferred into the wells at a concentration of 2×10$^5$ cells per 200 µl cell culture medium. Cells are incubated for 24 h at 37° C., 5% CO$_2$. Cell-free supernatant is then collected and analyzed for murine IL-2 using a mouse IL-2 ELISA kit (Bender MedSystems, #BMS601) following the manufacturers' instructions. IL-2 levels directly correlate with the degree of activation.

In a preferred embodiment, the polypeptide of the present disclosure is a monoclonal antibody. "Monoclonal antibody" as used herein means that the antibody comprises identical CDRs, thereby recognizing identical epitope(s). Usually, monoclonal antibodies are produced recombinantly using hybridoma technology, as generally known in the art. While the human IgG$_4$ monoclonal antibody of the present disclosure binds to human CD32b/c via its heavy chain Fc part, and is capable of activating same on CD32b/c expressing cells, in a preferred embodiment said antibody does not recognize the human CD32b/c receptor via its antigen binding regions, i.e. it does not recognize an epitope of human CD32b/c. Instead, the monoclonal antibody exhibits specificity for a different antigen. In certain embodiments, the monoclonal antibody may be bispecific. This means that each of the two antigen binding region may bind to a different epitope of the same antigen or to a different epitope on a different antigen. In accordance with the foregoing disclosure, the antibody disclosed herein may be a bispecific, trifunctional antibody; or the antibody said antibody may be a bispecific, bifunctional antibody. In certain embodiments, the monoclonal antibody is unmodified, and in particular not fused to a bioactive peptide amino acid sequence which acts as the pharmaceutically active agent, as e.g. described in WO 2014/144542 A2.

However, in preferred embodiments, the monoclonal antibody is a monospecific antibody. As a monospecific monoclonal antibody, the human IgG$_4$ antibody of the present disclosure will bind the same epitope with both antigen binding regions, i.e. the antibody has only one singular specificity.

In preferred embodiments, the antibody of the present disclosure binds to a cell surface receptor which is typically also present on the CD32b/c expressing cell. An antibody with such specificity may be able to cross-link CD32b/c along with said cell surface receptor, or at least co-localize the inhibitory CD32b/c receptor with said cell surface receptor in order to possibly down-modulate any activation of the cell surface receptor.

For example, the antibody bearing the mutant IgG$_4$ constant region of the present disclosure could be chemically, covalently or non-covalently multimerized in a way that enables cross-linking of CD32b/c on CD32b/c expressing cells without the need for immune complex formation.

The antibody may bind to an epitope on the cell surface on CD32b/c expressing cell (e.g. PDC, monocyte, B cell, myeloid DC and others), thereby being immobilized and at the same time binding and cross-linking the CD32b/c receptor through its mutant IgG$_4$ constant region as described herein, thereby inhibiting activation of the given cell and/or inducing regulatory phenotype. Cross-linking of any antibody bearing the human IgG$_4$ constant region of the present disclosure and formation of immune complexes by anti-drug antibodies may introduce a beneficial effect in autoimmune setting by cross-linking CD32b/c by the means of the mutant IgG$_4$ constant region disclosed herein, thereby inhibiting activation of B cells or other CD32b/c expressing cells (e.g. monocytes, myeloid or plasmacytoid DCs).

Alternatively, the polypeptide or monoclonal antibody of the invention may be designed such that it interacts with another cell which normally interacts with the CD32b/c expressing cell. An antibody bearing the human IgG$_4$ constant region of the present disclosure may be immobilized upon binding to its target epitope on the surface of any kind of cell (e.g. hematopoietic cell subsets, endothelial cells, epithelial cells and others). Then, upon cell-cell contact between cell expressing the epitope of the IgG$_4$ antibody and the cell expressing CD32b/c, the antibody may cross-link the CD32b/c on the surface of the CD32b/c expressing cell, thereby inhibiting activation of the CD32b/c expressing cell.

In a preferred embodiment, the antibody recognizes an epitope of a cell surface receptor selected from CD303 (also known as BDCA-2), CD304, ILT7, and CD123, as they can be found on the cell surface of PDCs. In other preferred embodiments, the antibody is directed against a cell surface molecule or receptor on B cells. For example, the antibody may recognize an epitope of a cell surface receptor selected from CD19, CD20, the B cell receptor (BCR), CD79A, and CD79B. In still other preferred embodiments, the antibody recognizes an epitope of a cell surface receptor or molecule on a monocyte. In particular, the antibody of the present disclosure may recognize an epitope selected from CD14 and CD11c. In still another preferred embodiment, the antibody recognizes an epitope of a cell surface receptor selected from CD141 and CD11c.

In a most preferred embodiment, the antibody recognizes an epitope of BDCA-2 (CD303). An example of such an antibody is the monoclonal antibody MB101. Said antibody is, for example, obtainable from the hybridoma deposited under the accession number DSM ACC3237 on 24 Apr. 2014 by Miltenyi Biotec GmbH, Bergisch Gladbach at the DSMZ (German Collection of Microorganisms and Cell Cultures) in Braunschweig, Germany, and represents another preferred embodiment of the present disclosure. In accordance with the monoclonal antibody MB101, the antibody of the present disclosure may comprises the heavy chain CDRs 1-3 shown in SEQ ID NOs: 2-4 and light chain CDRs 1-3 shown in SEQ ID NOs: 5-7. Even more preferably, the antibody of the present disclosure may comprise the variable heavy chain of SEQ ID NO: 8 and the variable light chain of SEQ ID NO: 9. As shown in Example 5, data of a phase I clinical trial appears to support a curative effect of MB101 in an autoimmune disease such as psoriasis.

In a further aspect, the present disclosure further pertains to a polypeptide comprising at least one human IgG$_4$ with a lysine at position 409 (409K) using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of allergy in a human subject, as further defined in the claims. As far as it makes technical sense, preferred embodiments of the above-described first aspect with regard to the polypeptide of the present disclosure apply likewise to this second aspect. In particular, the human IgG$_4$ with a lysine at position 409 (409K using the EU index according to Kabat et al.) described herein is capable of binding to human CD32b/c with a higher binding affinity of at least 2-fold, preferably at least 5-fold and most preferably at least 10-fold than the binding affinity of a wild-type human IgG$_1$ and/or a wild-type human IgG$_4$, as determined by using the above assay. In a preferred embodiment, the human IgG$_4$ further comprises a proline at position 241 (241 P), using the EU index according to Kabat et al. It is believed that this additional substitution further stabilizes the IgG$_4$ molecule. Accordingly, in a particularly preferred embodiment, the human IgG$_4$ comprises the amino acid sequence of SEQ ID NO: 1 (hIgG4) with a lysine at the position corresponding to position 409 (409K) and a proline at the position corresponding to position 241 (241 P), using the EU index according to Kabat et al. As described above, the polypeptide may be a fusion protein, in particular a fusion protein comprising two human IgG$_4$ Fc parts of the present disclosure, or a human IgG$_4$ Fc in fusion with a human IgG$_1$ or a human IgE. Still, in a further preferred that the polypeptide is a monoclonal antibody. While it is possible that such a monoclonal antibody is designed to bind to CD32b/c via its antigen binding regions, in preferred embodiments the monoclonal antibody described herein does not recognize an epitope of human CD32b/c via its antigen binding regions. Rather, in the context of the treatment of allergen, the antibody may recognize an epitope of IgE. For example, the antibody may exhibit the CDRs or variable binding regions of anti-IgE monoclonal antibody Xolair®. Alternatively, the antibody may recognize an epitope of a cell surface receptor selected from CD14 and CD11c; or a cell surface receptor selected from CD141 and CD11c. Hence, in certain embodiments, the antibody recognizes an epitope of a cell surface receptor selected from CD303, CD304, ILT7, CD123, CD19, CD20, the B cell receptor (BCR) such as IgE, CD79A, CD79B, CD14, CD11c, and CD141.

The present disclosure is further described by the following embodiments.

1. A polypeptide comprising at least one human IgG$_4$ with a lysine at position 409 (409K), using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of an autoimmune disease in a human subject.
2. The polypeptide for use of embodiment 1, wherein the autoimmune disease is an inflammatory autoimmune disease.
3. The polypeptide for use of any one of embodiment 1 or 2, wherein the autoimmune disease is further characterized by increased plasma levels of autoantibodies as compared to healthy subjects.
4. The polypeptide for use of any one of embodiments 1-3, wherein the autoimmune disease is selected from the group consisting of systemic lupus erythematosus, psoriasis, multiple sclerosis, and rheumatoid arthritis.
5. The polypeptide for use of any one of embodiments 1-4, wherein the autoimmune disease is systemic lupus erythematosus or psoriasis.
6. The polypeptide for use of any one of embodiments 1-5, wherein the human IgG$_4$ further comprises a proline at position 241 (241 P), using the EU index according to Kabat et al.
7. The polypeptide for use of any one of embodiments 1-6, wherein the human IgG$_4$ comprises the amino acid sequence of SEQ ID NO: 1 (hIgG$_4$) with a lysine at the position corresponding to position 409 (409K) and a proline at the position corresponding to position 241 (241P), using the EU index according to Kabat et al.
8. The polypeptide for use of any one of embodiments 1-7, wherein the human IgG$_4$ 409K 241 P shows an increased activation of human CD32b/c as compared to wt human IgG$_4$ and/or wt human IgG$_1$.
9. The polypeptide for use of any one of embodiments 1-8, wherein the polypeptide is a monoclonal antibody.
10. The polypeptide for use of embodiment 9, wherein the monoclonal antibody does not recognize an epitope of human CD32b/c via its antigen binding region.
11. The polypeptide for use of embodiment 9 or 10, wherein the monoclonal antibody is a monospecific antibody.
12. The polypeptide for use of any one of embodiments 1-11, wherein the antibody recognizes an epitope of a cell surface receptor selected from CD303, CD304, ILT7, and CD123.
13. The polypeptide for use of any one of embodiments 1-11, wherein the antibody recognizes an epitope of a cell surface receptor selected from CD19, CD20, the B cell receptor (BCR), CD79A, and CD79B.
14. The polypeptide for use of any one of embodiments 1-11, wherein the antibody recognizes an epitope of a cell surface receptor selected from CD14 and CD11c.
15. The polypeptide for use of any one of embodiments 1-11, wherein the antibody recognizes an epitope of a cell surface receptor selected from CD141 and CD11c.
16. The polypeptide for use of embodiment 12, wherein the antibody recognizes an epitope of BDCA-2 (CD303).
17. The polypeptide for use of embodiment 16, wherein the antibody comprises the heavy chain CDRs 1-3 shown in SEQ ID NOs: 2-4 and light chain CDRs 1-3 shown in SEQ ID NOs: 5-7.
18. The polypeptide for use of embodiment 17, wherein the antibody comprises the variable heavy chain of SEQ ID NO: 8 and the variable light chain of SEQ ID NO: 9.
19. The polypeptide for use of any one of embodiments 1-10 or 12-18, wherein the antibody is a bispecific, trifunctional antibody; or wherein the antibody is a bispecific, bifunctional antibody.
20. The polypeptide for use of any one of embodiments 1-19, wherein the human subject shows a dysregulation of CD32b expression, as compared to healthy subjects.
21. The polypeptide for use of any one of embodiments 1-20, wherein the human subject has a CD32b 695T allele and/or a 2B.4 haplotype of the CD32b gene.
22. The polypeptide for use of any one of embodiments 1-20, wherein the human subject has a CD32b 695C allele and/or a 2B.1 haplotype of the CD32b gene.
23. A polypeptide comprising at least one human IgG$_4$ with a lysine at position 409 (409K) using the EU index according to Kabat et al., which IgG$_4$ is capable of binding to human CD32b/c with a statistically significant (p=0.05) higher binding affinity than a wild-type human IgG$_1$ and than a wild-type human IgG$_4$, for use in the activation of human CD32b/c on CD32b/c expressing cells in the prevention and/or treatment of allergy in a human subject.
24. The polypeptide for use of any one of embodiment 23, wherein the human IgG$_4$ further comprises a proline at position 241 (241 P), using the EU index according to Kabat et al.
25. The polypeptide for use of embodiment 23 or 24, wherein the human IgG$_4$ comprises the amino acid sequence of SEQ ID NO: 1 (hIgG4) with a lysine at the position corresponding to position 409 (409K) and a proline at the position corresponding to position 241 (241 P), using the EU index according to Kabat et al.
26. The polypeptide for use of any one of embodiments 23-25, wherein the polypeptide is a monoclonal antibody.
27. The polypeptide for use of embodiment 26, wherein the monoclonal antibody does not recognize an epitope of human CD32b/c via its antigen binding region.
28. The polypeptide for use of embodiment 26 or 27, wherein the antibody recognizes an epitope of IgE.
29. The polypeptide for use of embodiment 26 or 27, wherein the antibody recognizes an epitope of a cell surface receptor selected from CD14 and CD11c.
30. The polypeptide for use of embodiment 26 or 27, wherein the antibody recognizes an epitope of a cell surface receptor selected from CD141 and CD11c.

31. The polypeptide for use of embodiment 26 or 27, wherein the antibody recognizes an epitope of a cell surface receptor selected from CD303, CD304, ILT7, CD123, CD19, CD20, the B cell receptor (BCR) such as IgE, CD79A, CD79B, CD14, CD11c, and CD141.

32. A human $IgG_4$ with a lysine at position 409 (409K using the EU index according to Kabat et al.), which $IgG_4$ is capable of binding to human CD32b/c with a higher binding affinity of at least 2-fold, preferably at least 5-fold and most preferably at least 10-fold than the binding affinity of a wild-type human $IgG_1$ and/or a wild-type human $IgG_4$, for use in the activation of human CD32b/c on CD32b/c expressing cells in the prevention and/or treatment of an autoimmune disease in a human subject.

33. The human $IgG_4$ for use of embodiment 32, as further defined by above embodiments 2-22.

34. A human $IgG_4$ with a lysine at position 409 (409K using the EU index according to Kabat et al.), which $IgG_4$ is capable of binding to human CD32b/c with a higher binding affinity of at least 2-fold, preferably at least 5-fold and most preferably at least 10-fold than the binding affinity of a wild-type human $IgG_1$ and/or a wild-type human $IgG_4$, for use in the activation of human CD32b/c on CD32b/c expressing cells in the prevention and/or treatment of allergy in a human subject.

35. The human $IgG_4$ for use of embodiment 34, as further defined by above embodiments 24-31.

The present invention is further illustrated in the following Examples and Figures, which are not intended to be understood as to limit the invention as defined by the claims.

---

DESCRIPTION OF THE SEQUENCES

Figure 1:
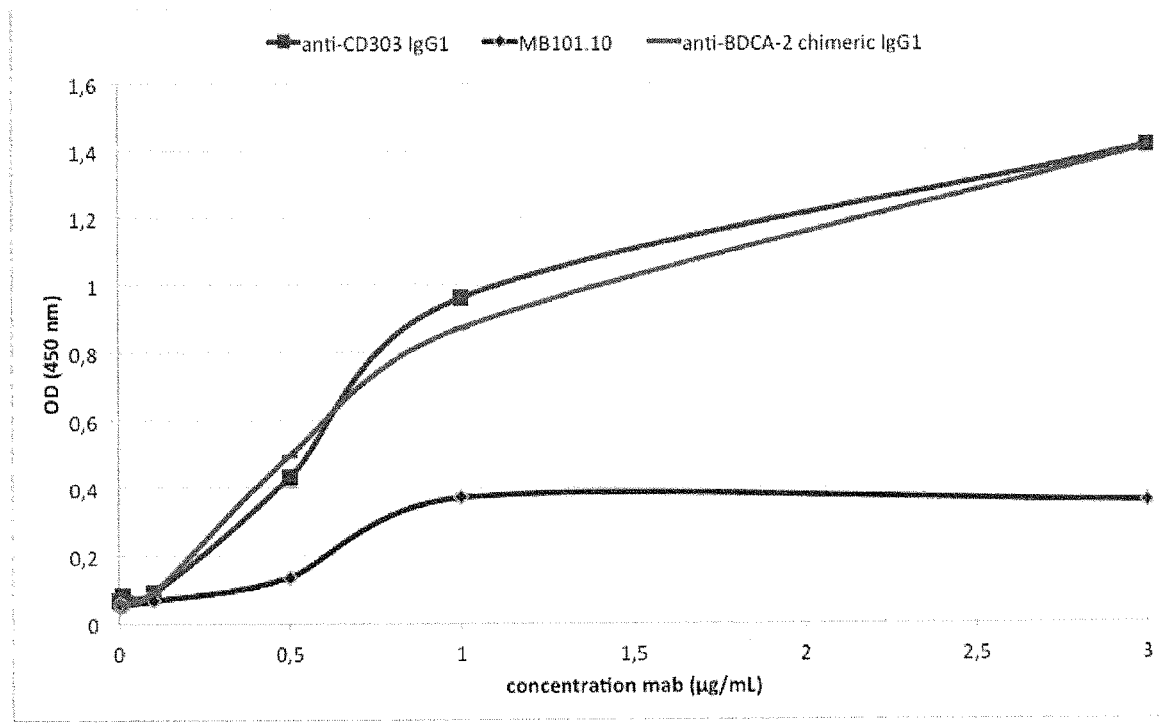
FIG. 1 shows the binding affinity of different $IgG_1$ mAbs and MB101 to recombinant human FcγRI (CD64) receptor (plate bound). It can be observed, that both $IgG_1$ variants have a high affinity to CD64, as expected for $IgG_1$ monoclonal antibodies. MB101 has a significantly lower affinity for CD64, which is also not surprising as MB101 is a humanized $IgG_4$ molecule for which lower affinities to CD64 are reported, compared to $IgG_1$ molecules

SEQ ID NO: 1-Human IgG$_4$ heavy chain constant region (CH1-hinge-CH2-CH3; accession number UNIPROT P01861-1; S241 and R409 are emphasized)

```
          10         20         30         40         50
ASTKGPSVFP LAPCSRSTSE STAALGCLVK DYFPEPVTVS WNSGALTSGV 60         70         80         90        100
HTFPAVLQSS GLYSLSSVVT VPSSSLGTKT YTCNVDHKPS NTKVDKRVES 110        120        130        140        150
KYGPPCPSCP APEFLGGPSV FLFPPKPKDT LMISRTPEVT CVVVDVSQED 160        170        180        190        200
PEVQFNWYVD GVEVHNAKTK PREEQFNSTY RVVSVLTVLH QDWLNGKEYK 210        220        230        240        250
CKVSNKGLPS SIEKTISKAK GQPREPQVYT LPPSQEEMTK NQVSLTCLVK 260        270        280        290        300
GFYPSDIAVE WESNGQPENN YKTTPPVLDS DGSFFLYSRL TVDKSRWQEG 310        320
NVFSCSVMHE ALHNHYTQKS LSLSLGK
```

SEQ ID NO: 2-MB101 heavy chain CDR1
SGFSLSTSGMGVG

SEQ ID NO: 3-MB101 heavy chain CDR2
HIWWEDDKYYNPSLKS

SEQ ID NO: 4-MB101 heavy chain CDR3
TRNWDYYTMDY

SEQ ID NO: 5-MB101 light chain CDR1
RASQEISGYLS

SEQ ID NO: 6-MB101 light chain CDR2
YAASTLDS

SEQ ID NO: 7-MB101 light chain CDR3
LQYASYPPT

SEQ ID NO: 8-MB101 variable region heavy chain (CDRs emphasized)
QVTLKESGPTLVKPTQTLTLTCTFSGFSLSTSGMGVGWIRQPPGKALEWLA**HIWWEDDKYY
NPSLKSRLTITKDTSKNQVVLTMTNMDPVDTATYYCTRNWDYYTMDY**WGQGTTVTVSSAST
KGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPP SEQ ID NO: 9-MB101 variable region light chain (CDRs emphasized)
DIQMTQSPSSVSASVGDRVTITCRASQEISGYLSWYQQKPGKAIKRLIYAASTLDSGVPSR
FSGSRSGTDFTLTISSLQSEDFATYYCLQYASYPPTFGGGTKLEIKGTVAAPSVFIFPPSD
EQLKSGTASVVCLLNNFYPREAKVQWKVDNALQSGNSQESVTEQDSKDSTYSLSSTLTLSK
ADYEKHKVYACEVTHQGLSSPVTKSFNRGEC SEQ ID NO: 10-Human IgG$_1$ heavy chain constant region (CH1-hinge-CH2-CH3; GenBank accession number AAC82527.1)
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVF
SCSVMHEALHNHYTQKSLSLSPGK

EXAMPLES

Example 1—Fc Receptor Binding Characteristics of MB101

In this example, different mAb were analyzed with regard to their ability to interact with five human Fcγ receptors CD16a CD16b/c, CD32a, CD32b and CD64. Two mutations (S241 P and R409K) were introduced into the human IgG$_4$ antibody MB101 for stability purposes. MB101 is a recombinant humanized therapeutic monoclonal IgG$_4$ antibody directed against CD303. MB101 was originally designed as a IgG$_4$ therapeutic antibody in order to exhibit no or significantly reduced effector functions. In order to evaluate the ADCC (antibody dependent cell cytotoxicity) and CDC (complement derived cytotoxicity)-potential via CD16 and CD64, MB101 was characterized for its binding to these receptors.

Despite not relevant for ADCC and CDC, MB101 (aCD303-hIgG$_4$-S241P/R409K) was also tested for its binding to human Fcγ receptors CD32a and CD32b/c. As MB101 was intended and designed as humanized IgG$_4$ molecule with stabilization, it was expected that MB101 behaves as typical IgG$_4$ molecule and shows no affinity or functional interactions with human Fcγ receptors like CD16A, CD32a, CD32b/c and CD64.

Fc receptor binding characteristics were analyzed in vitro in comparison to chimeric IgG$_1$ antibody variants of MB101 by evaluating the binding profile of to recombinant plate bound human recombinant Fcγ receptors (FcγR) CD16a, CD32a, CD32b/c and CD64.

Abbreviations

ADCC: antibody dependent cell cytotoxicity
ELISA: enzyme-linked immunosorbent assay
Fc: fragment crystallizable (of an Ab)
HRP: Horse-radish peroxidase
ITAM: immunoreceptor tyrosine-based activation motif
ITIM: immunoreceptor tyrosine-based inhibition motif
mAb: monoclonal antibody
PBS: phosphate buffered saline
RT: room temperature
SD: standard deviation
TMB: 3,3',5,5'-Tetramethylbenzidine
Material/Equipment
MB101.10 IgG$_4$ antibody (SAP 320-002-807, L/N A303P022) recombinant chimeric anti-CD303 (BDCA-2) IgG$_1$ wildtype (Cor 6.10.11) chimeric anti-BDCA2 IgG$_1$ (FE 060620.02)

MB101.10 (L/N A303P022) is a humanized IgG$_4$ antibody directed against BDCA-2 (CD303) and intended for clinical applications. Beside this version of MB101, a chimeric anti-BDCA-2 IgG$_1$ antibody generated in chimeric mice (hybridoma) and a recombinant chimeric anti-CD303 (BDCA-2) IgG1 antibody (AC144 binding region with human Fc region) were used. Mb101.10 was manufactured in CHO DG44 cells, recombinant chimeric anti-CD303 (BDCA-2) IgG$_1$ was manufactured in HEK293.EBNA cells and chimeric anti-BDCA-2 IgG$_1$ antibody was derived from hybridoma cells.
Fcγ Receptors:
Recombinant Human Fc gamma RI/CD64, R&D Systems, 1257-FC-050
Recombinant Human Fc gamma RIIa/CD32a, R&D Systems, 1330-CD-050
Recombinant Human Fc gamma RIIb/CD32b) R&D Systems, 1875-CD-050
Recombinant Human Fc gamma RIIIa/CD16a, R&D Systems, 4325-FC-050
Recombinant Human Fc gamma RIIIb/CD16b, R&D Systems, 1597-FC-050
Method ELISA plates were coated with Fc gamma receptors I, IIa, IIb, IIIa and IIIb with 5 μg/mL each in coating buffer overnight at 4° C. Coated plates were washed 3-fold with 1×PBS 0.05% Tween 20 and blocked with 5% BSA in 1×PBS. Antibodies were applied to ELISA plates with 50 μL/well at serial 2-fold dilution of antibody solution and incubated at room temperature for 1 h. As blank controls, respective antibody concentrations were also applied to wells lacking coated Fc gamma receptors, in order to substract unspecific binding from resulting signals. After washing (see above), the detection antibody anti-human kappa-HRP (FE 110316.07) 1:4000 in 1×PBS was applied with 50 μL/well and incubated again at RT for 1 h. After additional washing (see above), for assay development 50 μL/well TMB (CH111027.37) were applied and stopped after approx. 5 minutes with 50 μL/well 10% H$_2$SO$_4$. The developed plate was then analyzed via ELISA reader at 450 nm wavelength.
Results With regard to the binding to Fcγ RI (CD64, High Affinity Fc gamma Receptor), FIG. 1 shows that both IgG$_1$ variants have a high affinity to CD64, as expected for IgG$_1$ monoclonal antibodies. MB101 has a significantly lower affinity for CD64, which is also not surprising as MB101 is a humanized IgG$_4$ molecule for which lower affinities to CD64 are reported, compared to IgG$_1$ molecules. It has to be noted that MB101 still has a minimal affinity to CD64.

Figure 2:
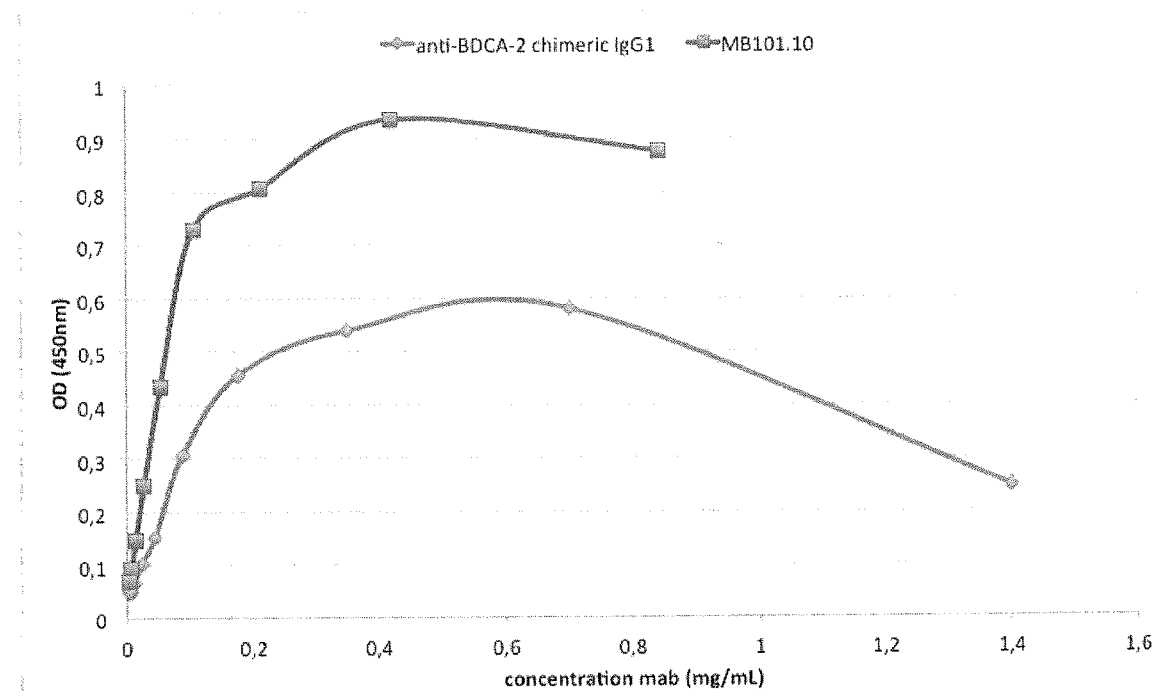
FIG. 2 shows the binding affinity of a chimeric $IgG_1$ mAb and MB101.10 to recombinant human FcγRIIa (CD32a) receptor (plate bound). It can be observed that MB101 has a moderately higher affinity for CD32a compared to the chimeric $IgG_1$ molecule.

With regard to the binding to Fcγ RIIa (CD31a, Low Affinity Fc gamma Receptor), FIG. 2 shows that MB101 has a moderately higher affinity for CD32a compared to the chimeric IgG$_1$ molecule.

Figure 3:
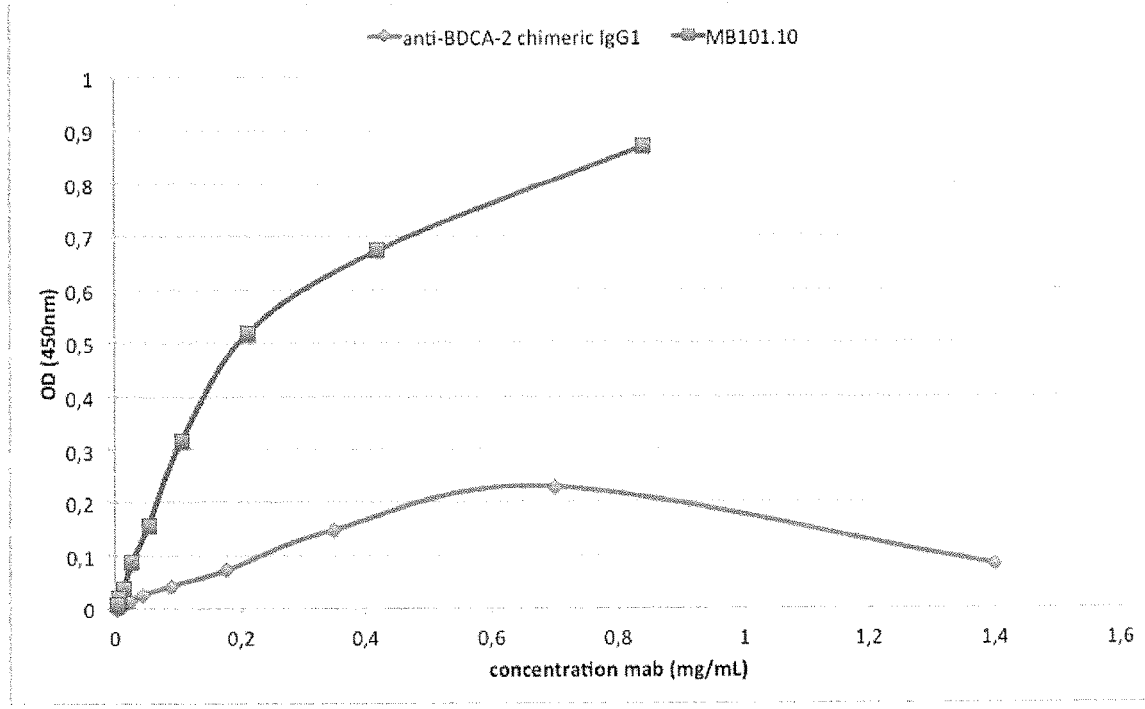
FIG. 3 shows the binding affinity of an chimeric $IgG_1$ mAb and MB101 to recombinant human FcγRIIb (CD32b) receptor (plate bound). It can be observed that MB101 has a significantly higher affinity for CD32b receptor compared to the chimeric $IgG_1$ molecule.

With regard to the binding to Fcγ RIIb (CD31b, Low Affinity Fc gamma Receptor), FIG. 3 shows that MB101 has a significantly higher affinity for CD32b receptor compared to the chimeric IgG$_1$ molecule.

Figure 4:
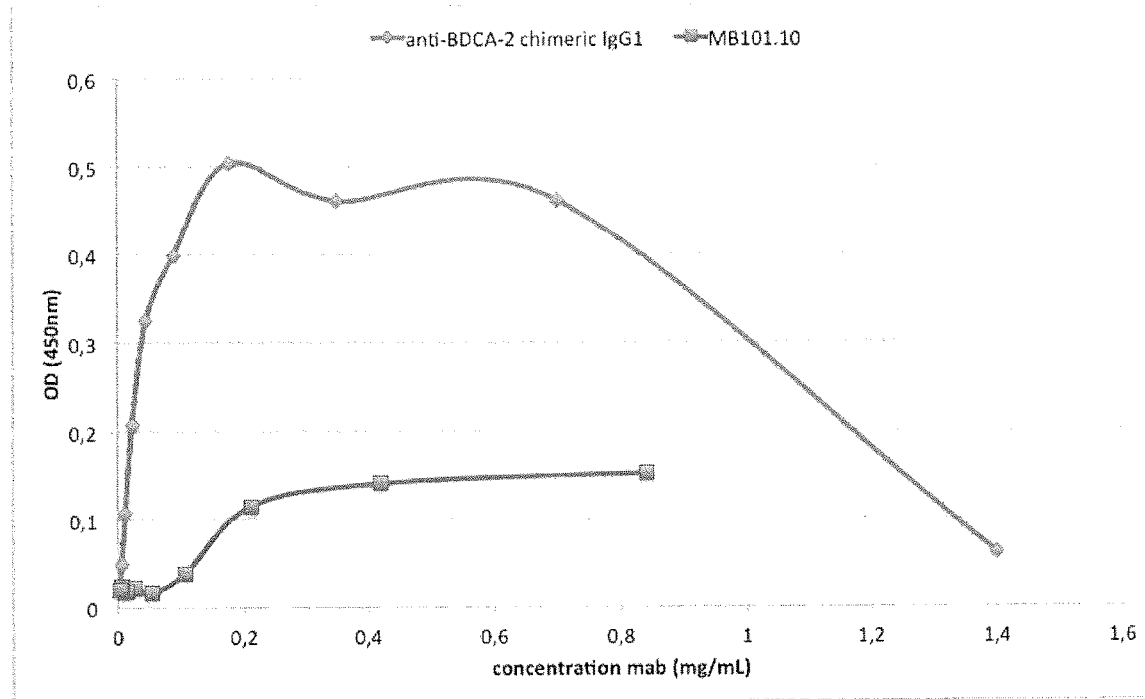
FIG. 4 shows the binding affinity of an chimeric $IgG_1$ mAb and MB101.10 to recombinant human Fcγ RIIIa (CD16a) receptor (plate bound). It can be observed that MB101 has a significantly lower affinity for CD16a compared to the chimeric $IgG_1$ molecule. A minimal residual binding affinity to CD16a can still be found.

With regard to the binding to Fcγ RIIIa (CD16a, Low Affinity Fc gamma Receptor), FIG. 4 shows that MB101 has a significantly lower affinity for CD16a compared to the chimeric IgG$_1$ molecule. A minimal residual binding affinity to CD16a can still be found.

Figure 5:
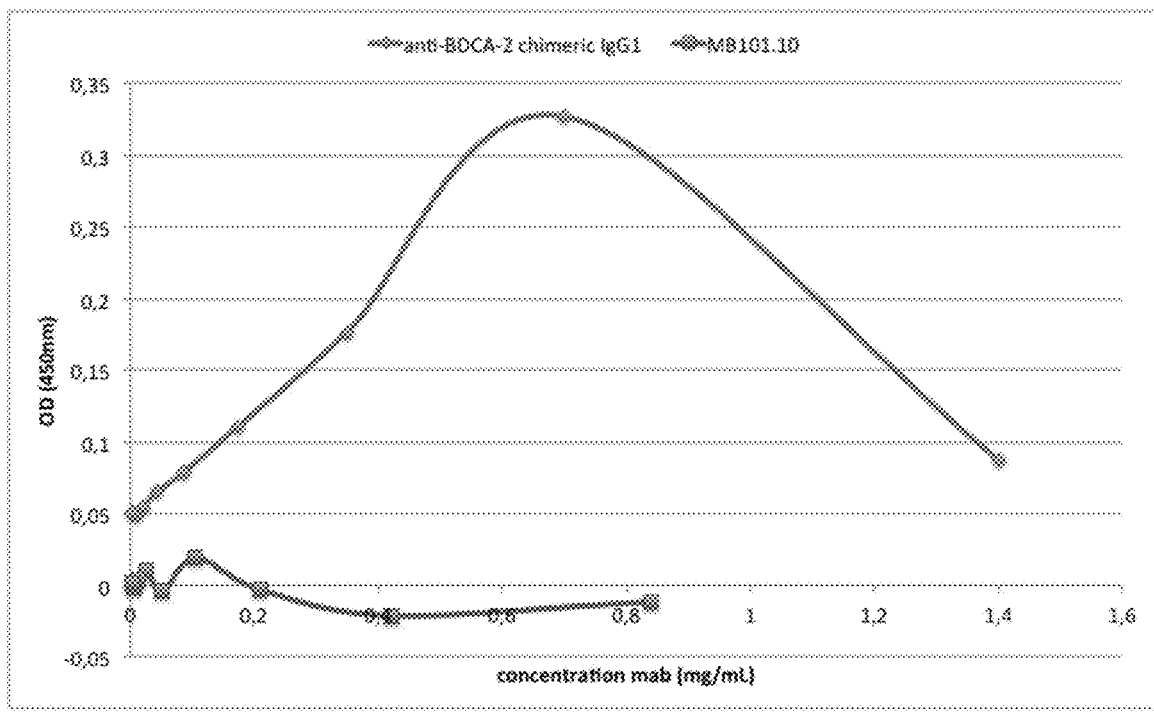
FIG. 5 shows the binding affinity of an chimeric $IgG_1$ mAb and MB101.10 to recombinant human Fcγ RIIIb/c (CD16b/c) receptor (plate bound). It can be observed that MB101 has no affinity for CD16b/c. In comparison, the chimeric $IgG_1$ molecule has a medium binding affinity to CD16b/c.

With regard to the binding to Fcγ RIIIb/c (CD16b/c), FIG. 5 shows that MB101 has no affinity for CD16b/c. In comparison, the chimeric IgG1 molecule has a medium binding affinity to CD16b/c.

Conclusions

Clear differences in FcγR interactions could be observed for the different tested receptors. The interactions of MB101 with CD16a, CD16b/c and CD64 were significantly lower than the compared chimeric anti-BDCA-2 IgG$_1$. The significantly lower affinity of MB101 for CD16a, CD16b/c and CD64 was an expected design feature of MB101 by the choice of using a human IgG$_4$ backbone without effector function. This design feature should reduce antibody interactions with effector cells (e.g. macrophages, monocytes and natural killer cells). As an effect of this low affinity and activation potential, a low or absent ADCC activity potential of MB101 is assumed and the intended design goal was achieved.

Interestingly, MB101 shows a notable affinity to CD32a and CD32b, which is moderately to significantly higher than the binding affinity of the chimeric anti-BDCA-2 $IgG_1$ and could not be expected from the choice of an human $IgG_4$ molecule or from the introduced stabilization mutations that change the $IgG_4$ molecule to a slightly $IgG_1$-ish human monoclonal antibody backbone. Surprisingly, it was found that the affinity of MB101 for the CD32a and CD32b receptors is even higher than for the $IgG_1$ control.

The Fcγ receptor FcγIIa (CD32a) has an activating ITAM (immunoreceptor tyrosine-based activation motif) and is found on monocytes, neutrophils, platelets and dendritic cells. Binding to this receptor may lead to activated cells via the ITAM. The affinity of MB101 to this receptor may therefore induce activation of B cells and dendritic cells. The Fcγ receptor FcγIIb (CD32b) has an inhibiting ITIM (immunoreceptor tyrosine-based inhibition motif) and is found on B cells and myeloid dendritic cells. Binding to this receptor may lead to inhibited cells via the ITIM. The affinity of MB101 to this receptor may therefore inhibit the antibody production of B cells and inhibit the maturation and cell activation of certain dendritic cells.

Example 2—Cell-Based In Vitro Assays for Functionality on CD32a and CD32b

The purpose of this set of experiments is to evaluate the activation profile of antibody MB101 on low-affinity human Fcγ receptors (FcγR) CD16A, CD32a and CD32b/c on recombinant stable transfected reporter cell lines in in vitro assays. The aim of this study is to evaluate the potency of MB101 to activate different FcγR expressing cells upon Fc-part mediated binding. A particular interest was to analyze potential interactions of MB101 with Fc receptors regarding binding affinity and receptor activity upon binding. Both wild-type $IgG_1$ and $IgG_4$ antibodies are used as controls in these assays.

In the human population several different allelic forms of low-affinity FcγRs are expressed, albeit at comparably low frequency. We tested IgG interactions with the following allelic forms of Fcγ receptors, CD16aV158 (FcγRIIIAV158), CD32aR131 (FcγRIIAR131) and CD32b/c (FcγRIIB/C). In case of CD16 two important allelic forms are found, CD16aF158 and CD16aV158 (amino acid sequence numbering according to Nimmerjahn, F., and Ravetch, J. V. 2008. Fc gamma receptors as regulators of immune responses. Nature Reviews Immunology 8: 34). We studied the more abundant allelic form of CD16, CD16aV158. In case of CD32 three different receptors are found that are encoded by three separate gene loci, CD32a, b and c. Although CD32b and CD32c exhibit different biological functions, they express identical extracellular amino acid sequences in amino-acid positions 43-217. Thus, to determine Fcγ interactions of CD32b and CD32c we used one transfectant expressing the extracellular domains of CD32b. In the following this clone is referred to as CD32b/c. In case of CD32a we expressed the allelic form CD32aR131, which is broadly found in the human population.

For the generation of transfectants the murine thymoma cell line BW5147 was used. For surface expression of the different Fcγ receptors fusion proteins were engineered consisting of the extracellular domain of the respective human FcγR portion linked with the transmembrane and intracellular ζ-chain of the murine T cell receptor. As BW5147 cells carry an intracellular response element that leads to the production of murine Interleukin (IL)-2 once a signal via the ζ-chain of the T cell receptor is conveyed, transfectants are expected to secrete murine IL-2 upon interaction of the expressed FcγRs with IgG. The amount of murine IL-2 production is supposed to be directly linked with the intensity of the interaction of IgG with the respective FcγR.

To test the ability of different mAbs to bind to and to cross-link the individual FcγRs, mAbs were coated to plastics and the transfectants were added. If a mAb interacted with a tested FcγR, murine IL-2 production was induced. Absolute IL-2 levels are taken as readout of Fcγ-FcγR-interaction. Tests with control mAbs allow comparative evaluation of interaction strength. This experimental setting is suited to study conditions of Fc-FcR-interactions that are also relevant in vivo, when a mAb is bound to a cell-surface target and interacts with Fc-receptors on different immune cells.

Abbreviations

ADCC: antibody dependent cell-mediated cytotoxicity
CD: cluster of differentiation
ELISA: enzyme-linked immunosorbent assay
Fc: fragment crystallizable (of an Ab)
FCS: fetal calf serum
IL: Interleukin
mAb: monoclonal antibody
PBS: phosphate buffered saline
RT: room temperature
SD: standard deviation
FcγR Transfectants BW5147-transfectants were used expressing fusion proteins consisting of the mouse ζ-transmembrane and cytoplasmic domains and the extracellular domains of CD16a, CD32a, or CD32b/c.

| Cell line | Referred to as | Plasmid |
| --- | --- | --- |
| BW5147 CD16A$_{V158}$-ζ | CD16a | pcDNAZ-CD16zeta |
| BW5147 CD32A$_{R131}$-ζ | CD32a | pcDNAZ-CD32Azeta |
| BW5147 CD32B-ζ | CD32b/c | pcDNAZ-CD32Bzeta |

Cell Culture Material for FcγR-Expressing Transfectants

| | | |
| --- | --- | --- |
| RPMI | Biochrom AG # F1215 | 500 ml |
| FCS (100%) | Sigma # F7524 | 10% |
| Glutamax (100x) | Invitrogen # 35050-038 | 1% |
| Sodium Pyruvate (100 mM) | Biochrom # AG L0473 | 1% |
| Zeocin (for selection) | Invitrogen # ant-zn-5b | 0.5 mg/ml end concentration |

Cells were passaged every 2-3 days in medium enriched with 0.5 mg/ml Zeocin.
Coating of Plastic with Antibody and Assay Procedure mAbs were serially 3-fold diluted in 1:10 (total log 3 dilution) in binding buffer (10 mM Bis-Tris, pH 6) starting with a concentration of 10 μg/ml. 100 μl of each dilution were transferred to a single well and the coating was performed over night at 4° C. After removal of the coating reagent, 200 μl per well blocking buffer (PBS+FCS 10%) were added and incubated for 1 h at RT. After blocking the wells were washed 3 times with 300 μl PBS. FcγR-expressing transfectants were transferred into the wells at a concentration of $2 \times 10^5$ cells per 200 μl cell culture medium. Cells were incubated for 24 h at 37° C., 5% $CO_2$. Cell-free supernatant was then collected and analyzed for murine IL-2 using a mouse IL-2 ELISA kit (Bender MedSystems, #BMS601) following the manufacturers' instructions.

Results

Figure 6:
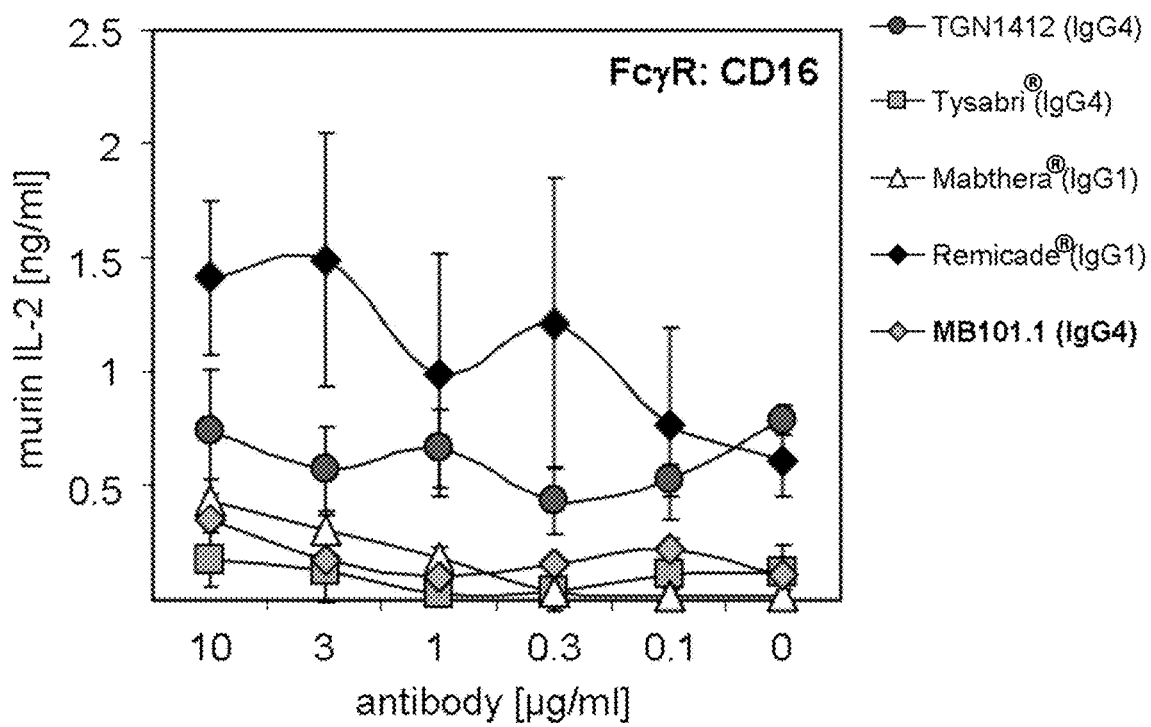
FIG. 6: Interaction of different mAbs with transfectants expressing the human FcγR $CD16_{V158}$. BW5147 transfectants expressing the FcγR CD16 were incubated with coated TGN1412 (dot), Tysabri® (square), Mabthera® (triangle), Remicade® (black diamond), or MB101 (blue diamond) at the indicated concentrations and murine IL-2 secretion was measured by an ELISA method (Bender MedSystems). Values are depicted as the mean of duplicate (MB101) or triplicate (TGN1412, Tysabri®, Mabthera®, and Remicade®) measurements±SD.

In order to quantify the interaction of different mAbs with human FcγRs, the antibodies TGN1412, Tysabri®, Mabthera®, Remicade®, and MB101 were coated in duplicates (MB101) or triplicates (TGN1412, Tysabri®, Mabthera®, and Remicade®) in log 3 dilutions ranging from 10 to 0.1 μg/ml. TGN1412, Tysabri®, and MB101 are IgG$_4$ mAb, whereas Mabthera® and Remicade® are IgG$_1$ mAb. As shown in FIG. 6, MB101 showed minor interactions with the low affinity FcγR CD16. The interaction of MB101 is comparable with the interaction of the other IgG$_4$ mAb Tysabri® and the IgG$_1$ mAb Mabthera®. Furthermore, interaction of MB101 with CD16-expressing transfectants is lower than those observed with the IgG$_4$ mAb TGN1412.

Figure 7:
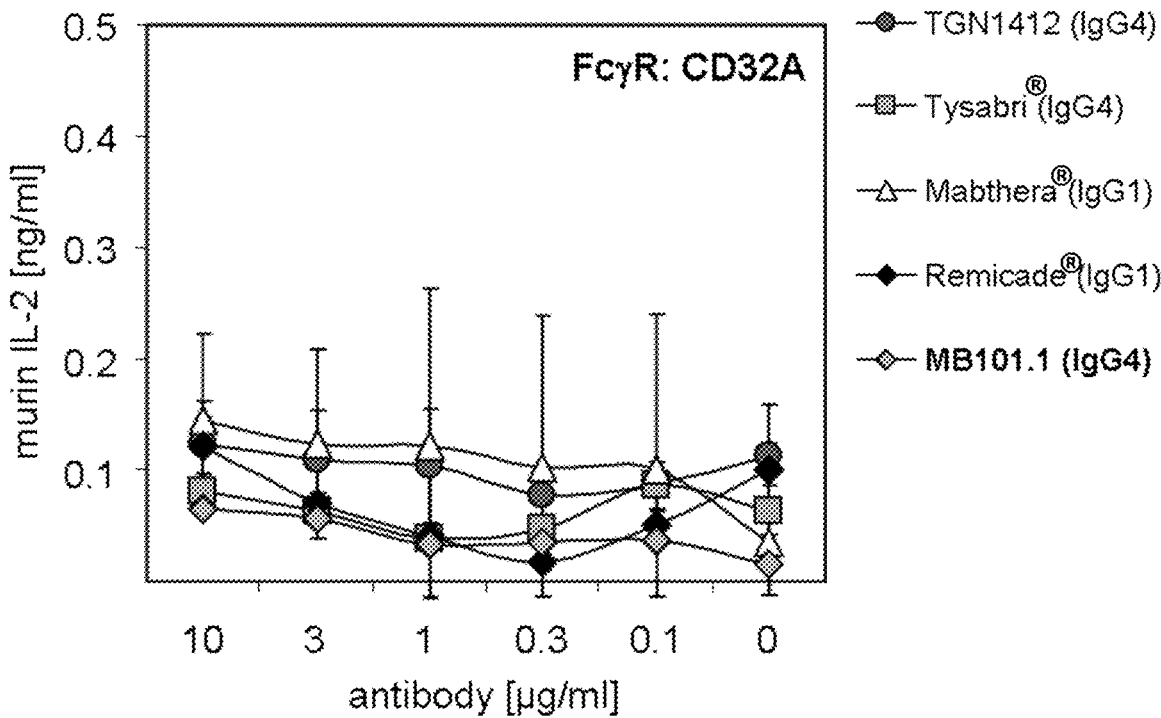
FIG. 7: Interaction of different mAbs with transfectants expressing the human FcγR CD32A. BW5147 transfectants expressing the FcγR CD32A were incubated with coated TGN1412 (dot), Tysabri® (square), Mabthera® (triangle), Remicade® (black diamond), or MB101 (blue diamond) at the indicated concentrations and murine IL-2 secretion was measured by ELISA (Bender MedSystems). Values are depicted as the mean of duplicate (MB101) or triplicate (TGN1412, Tysabri®, Mabthera®, and Remicade®) measurements±SD.

The mAb MB101 showed very minor interactions with FcγR CD32a expressing transfectants (FIG. 7) and are similar to those found with Tysabri® (IgG$_4$), Remicade® (IgG$_1$), TGN1412 (IgG$_4$) or Mabthera® (IgG$_1$). Activation profile data of MB101 on recombinant CD32a reporter cells shows that MB101 has no activation potential on CD32a (but binding potential, see above) and is judged only as binding, but not activating molecule on CD32a.

Figure 8:
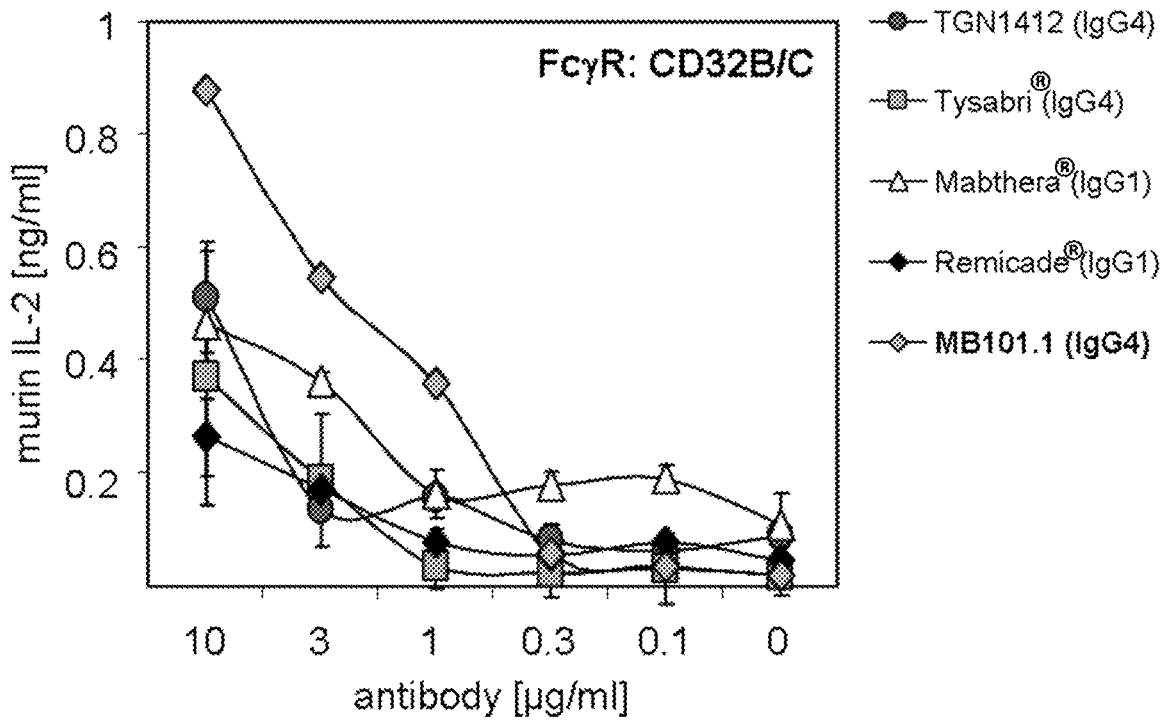
FIG. 8: Interaction of different mAbs with transfectants expressing the human FcγR CD32b/c. BW5147 transfectants expressing the FcγR CD32b/c were incubated with coated TGN1412 (dot), Tysabri® (square), Mabthera® (triangle), Remicade® (black diamond), or MB101 (blue diamond) at the indicated concentrations and murine IL-2 secretion was measured by ELISA (Bender MedSystems). Values are depicted as the mean of duplicate (MB101) or triplicate (TGN1412, Tysabri®, Mabthera®, and Remicade®) measurements±SD.

However, MB101 shows enhanced interaction with the CD32b/c-expressing transfectants when compared with the other IgG$_4$ mAbs (TGN1412 or Tysabri®) and IgG$_1$ mAbs (Mabthera® or Remicade®) (see FIG. 8). Cells were highly activated to secrete IL-2 as indicator for receptor mediated effects. Activation profile data of MB101 on recombinant CD32b reporter cells shows that MB101 has not only a significant binding activity, which is much higher than for IgG$_4$ and IgG$_1$ molecules, but also a significant activation potential on CD32b that is not found at this level for other tested IgG$_4$ and IgG$_1$ molecules. This activation capacity on the inhibitory ITIM receptor CD32b is expected to result in B cell and dendritic cell inhibition.

Conclusions

In this study, different mAb were analyzed with regard to their ability to interact with the low-affinity human FcγR CD16 (FcγRIIIA$_{V158}$), CD32a (FcγRIIA$_{R131}$) and CD32b/c (FcγRIIB). The typical high affinity CD64 (FcγRI) was not analyzed, as it would deliver not-comparable results due to the different nature (low vs. high-affinity receptor). Clear differences in FcγR interactions could be observed for the different tested mAb. The interactions of MB101 with CD16- and CD32a-expressing transfectants seemed to be lower than the interactions of TGN1412 and Remicade® with CD16 as well as TGN1412 and Mabthera® with CD32a. Compared with IgG$_1$ and IgG$_4$ mAbs, MB101 showed a highly enhanced interaction and activation on CD32b/c-expressing transfectants. This activation capacity on the inhibitory ITIM receptor CD32b is expected to result in B cell and dendritic cell inhibition.

Example 3—FcγR Interactions of MB101 and its Single Mutation Variants

Murine transfectants expressing the extracellular domains of human FcγRs were used to assess the multivalent interaction of mAb variants with different FcγRs. In the used system the interaction is measured by the release of murine IL-2 that is secreted into the supernatant after FcγR engagement of the transfectants. mAbs were coated to maxisorb 96 well plates at concentrations of 1 μg, 0.3 μg, 0.1 μg and 0.03 μg. In addition to MB101 (aCD303-hIgG4-S241P/R409K), two single mutation variants, Pool 3 (aCD303-hIgG4-S241P) and Pool 6 (aCD303-hIgG4-R409K), the wild type IgG$_4$ antibody (aCD303-hIgG$_4$), and other IgG$_4$ and IgG$_1$ control mAbs were tested. The antibodies were coated in binding buffer for 2 h at 37° C. and then blocked with 1% BSA for one hour at room temperature. 2×10$^5$ transfectants were added and incubated for 18 h at 37° C. before the supernatant was harvested and tested for murine IL-2 content by an ELISA method.

Figure 9:
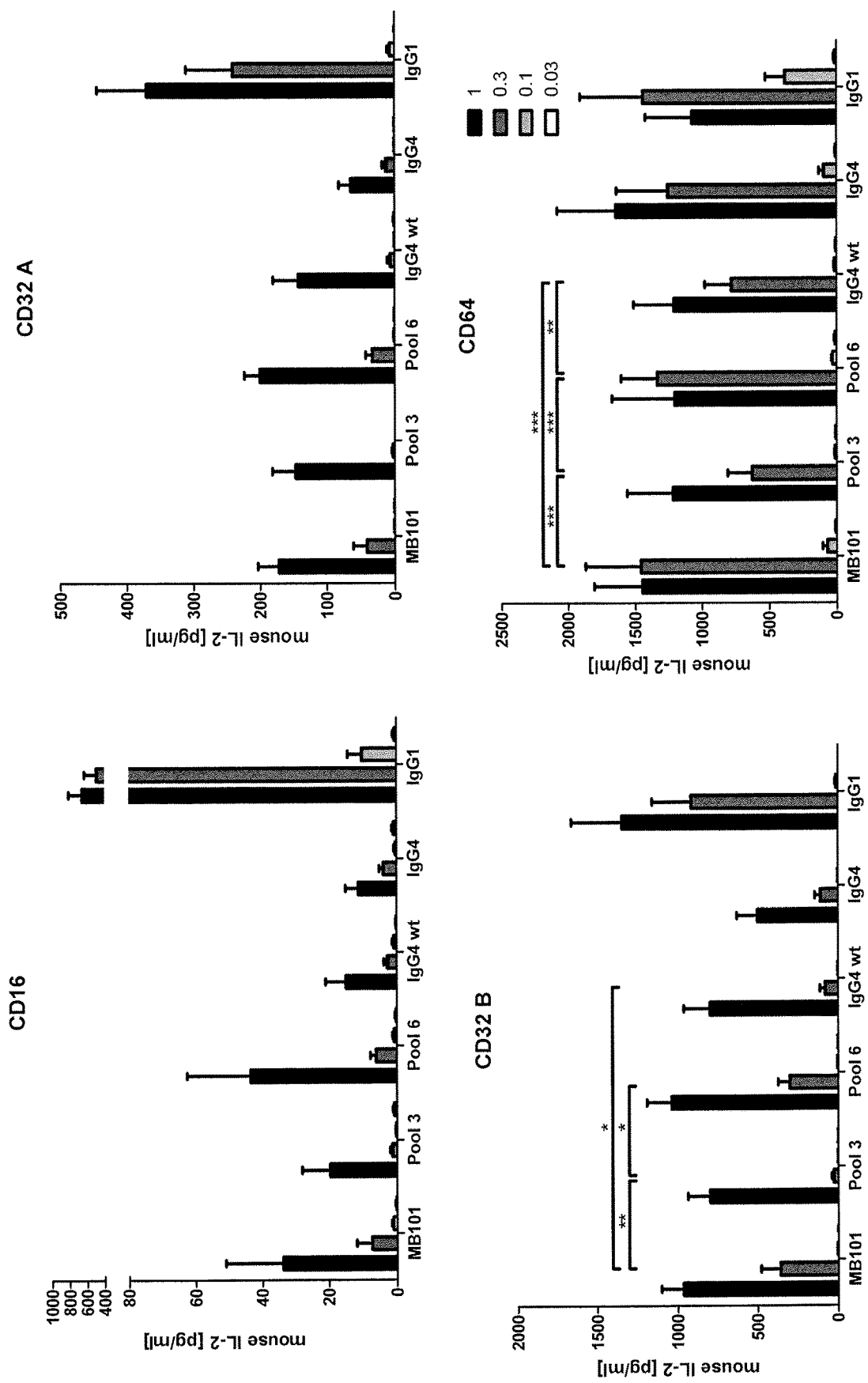
FIG. 9: A single amino acid exchange introduced into the constant region of MB101 (Pool 6; R409K) leads to a significantly increased binding to CD32b and CD64. MB101 (anti-CD303) expressed as a wild type $IgG_4$ and the two single mutation variants Pool 3 (anti-CD303 $IgG_4$ S241 P) and Pool 6 (anti-CD303 $IgG_4$ R409K) were coated in a log 3 serial dilution starting with 1 µg to 96 well plates in $Na_2HPO_4$ binding buffer for 2 h at 37° C. As controls, antibodies from the $IgG_4$ (TGN1412) and $IgG_1$ (BT-061) subclass were used. Then transfectants expressing one of the human FcγR were incubated on the coated plates for 18 h. Afterwards, cell-free supernatants were harvested and the mouse IL-2 content was analyzed by an ELISA method. N=5 with two biological duplicates for each value. Statistical analysis was performed using a two-way Anova with Bonferroni's multiple comparison test.

The results are shown in FIG. 9. IL-2 expression levels detected after incubation with the CD16 expressing transfectants revealed that the classical IgG$_1$ control antibody induced significant IL-2 expression, whereas the IgG$_4$ control, the wt IgG$_4$ antibody, and Pool 3 (aCD303-hIgG$_4$-S241 P) induce only minor amounts of IL-2 that further decreased with increased mAb dilution. The data obtained for Pool 6 (aCD303-hIgG$_4$-R409K) and MB101 (aCD303-hIgG$_4$-S241 P/R409K) suggest that there was a trend towards increased IL-2 expression, however, the data were not significant.

The data obtained with the CD32a expressing transfectants were overall rather similar for MB101 (aCD303-hIgG$_4$-S241P/R409K), the two variants and the wt antibody. The detected IL-2 levels were generally slightly higher than those of the IgG$_4$ control but clearly weaker than those of the IgG$_1$ control. Analyzing the induction of IL-2 after addition of the CD32b transfectant revealed a significant difference between MB101 (aCD303-hIgG$_4$-S241P/R409K) and Pool 6 (aCD303-hIgG$_4$-R409K) compared to Pool 3 (aCD303-hIgG$_4$-S241P) and the wt IgG$_4$. This difference was particularly evident at the coating concentration of 0.3 μg. This argues that the inclusion of a single mutation in the hinge region (Pool 6; aCD303-hIgG$_4$-R409K) leads to enhanced interaction with CD32b and therefore increased IL-2 production, shifting the IgG$_4$ FcγR binding profile towards that of an IgG$_1$. The enhanced CD32B interaction of Pool 6 (aCD303-hIgG$_4$-R409K) and MB101 (aCD303-hIgG$_4$-S241P/R409K) was similarly observed in experiments with the CD64 transfectant.

Figure 10:
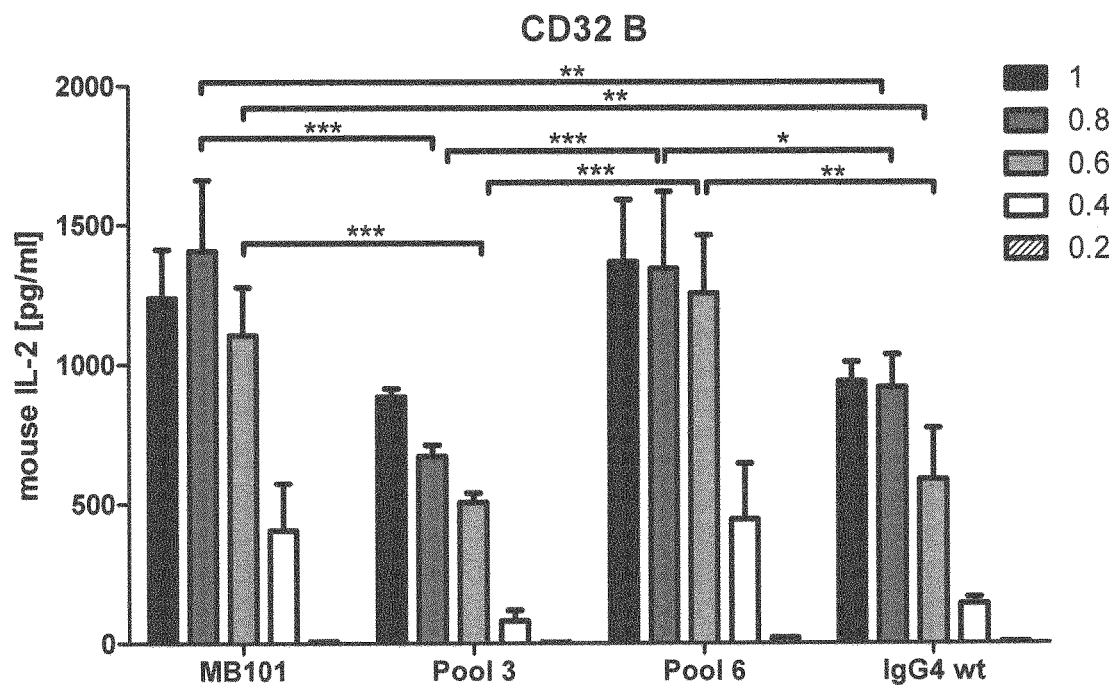
FIG. 10: MB101 (anti-CD303 $IgG_4$ S241 P/R409K) and Pool 6 (anti-CD303 $IgG_4$ R409K) induce CD32b expressing transfectants to produce significantly more IL-2 than Pool 3 (anti-CD303 $IgG_4$ S241 P) and the wt $IgG_4$. To examine more precisely the CD32b binding of MB101, the wt $IgG_4$ and the two single mutation variants, linear dilutions of the mAbs were coated to plates starting with 1 µg and incubated with the CD32b expressing transfectants. After 18 h supernatant was harvested and analyzed by an ELISA method. N=3 with two biological duplicates for each value. Statistical analysis was performed using a two-way Anova with Bonferroni's multiple comparison test.

To more closely analyze the interaction of MB101 (aCD303-hIgG4-S241P/R409K) with CD32B, the two MB101 variants and the wt antibody were coated at concentrations of 1 μg, 0.8 μg, 0.6 μg, 0.4 μg and 0.2 μg. The result is shown in FIG. 10. Also under such conditions MB101 (aCD303-hIgG$_4$-S241P/R409K) and Pool 6 (aCD303-hIgG$_4$-R409K) induced significantly more IL-2 production at concentration of 0.8 and 0.6 μg than Pool 3 (aCD303-hIgG$_4$-S241P) and the wt IgG$_4$. This further verified that a single mutation in the hinge region of the original IgG$_4$ antibody does indeed change the FcγR binding profile.

Figure 11:
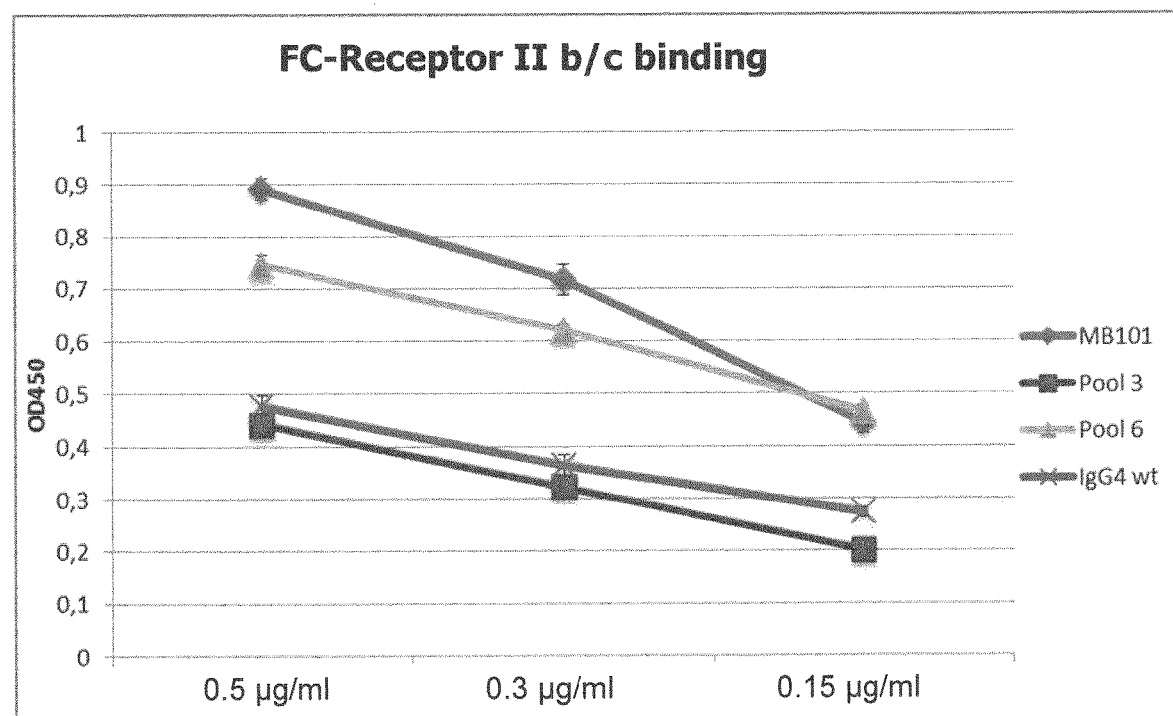
FIG. 11: MB101 (anti-CD303 $IgG_4$ S241 P/R409K) and Pool 6 (anti-CD303 $IgG_4$ R409K) show stronger binding to CD32b/c compared to Pool 3 (anti-CD303 $IgG_4$ S241 P) and the wt $IgG_4$. To examine more precisely the CD32b/c binding of MB101, the wt $IgG_4$ and the two single mutation variants, linear dilutions of the mAbs were incubated with ELISA plates previously coated with recombinant CD32b/c. FcR-bound anti-BDCA2 Ab were probed with anti-human kappa-HRP and TMB-substrate.

These data was further confirmed using a CD32a/b binding ELISA. To this end ELISA plates were coated with recombinant human FcγRIIb (CD32b) protein (R&D Reagents, Cat:1875-CD; Lot: GJZ0814031) and binding of MB101 (aCD303-hIgG$_4$-S241P/R409K), the wt MB101 and the two mutated variants Pool 3 (aCD303-hIgG$_4$-S241P) and Pool 6 (aCD303-hIgG$_4$-R409K) was probed. Similar to the data obtained from the previous experiment MB101 (aCD303-hIgG$_4$-S241 P/R409K) and Pool 6 variant (aCD303-hIgG$_4$-R409K) showed stronger binding to the recombinant human FcγRIIB/C than WT IgG$_4$ mAb and Pool 3 (aCD303-hIgG$_4$-S241P) as evident from the higher OD$_{450}$ values (FIG. 11).

To next validate whether the change in the FcγR binding profile of Pool 6 (aCD303-hIgG$_4$-R409K) also influenced the specific target binding of MB101 (aCD303-hIgG$_4$-S241P/R409K), we made use of a transfectant showing induced GFP expression upon engagement of BDCA-2 (kindly provided by Miltenyi). This allows testing whether the increased binding of MB101 (aCD303-hIgG$_4$-S241P/R409K) and Pool 6 (aCD303-hIgG$_4$-R409K) to CD32B also leads to more abundant BDCA-2 triggering as measured by a stronger GFP expression in the transfectants compared with the induction of Pool 3 (aCD303-hIgG$_4$-S241P) and the wt antibody.

Therefore, 1×10$^5$ CD32b or the control CD99 transfectant were seeded in a 96 well plate in 100 µl medium. MB101 (aCD303-hIgG$_4$-S241P/R409K), Pool 3 (aCD303-hIgG$_4$-S241P), Pool 6 (aCD303-hIgG$_4$-R409K) and the wt antibody were added at concentrations of 0.5, 0.1, 0.05, 0.04, 0.03, 0.02 and 0.01 µg. Then 1×10$^5$ BDCA-2 transfectants were added and the cells were co-cultured for 24 h.

Figure 12:
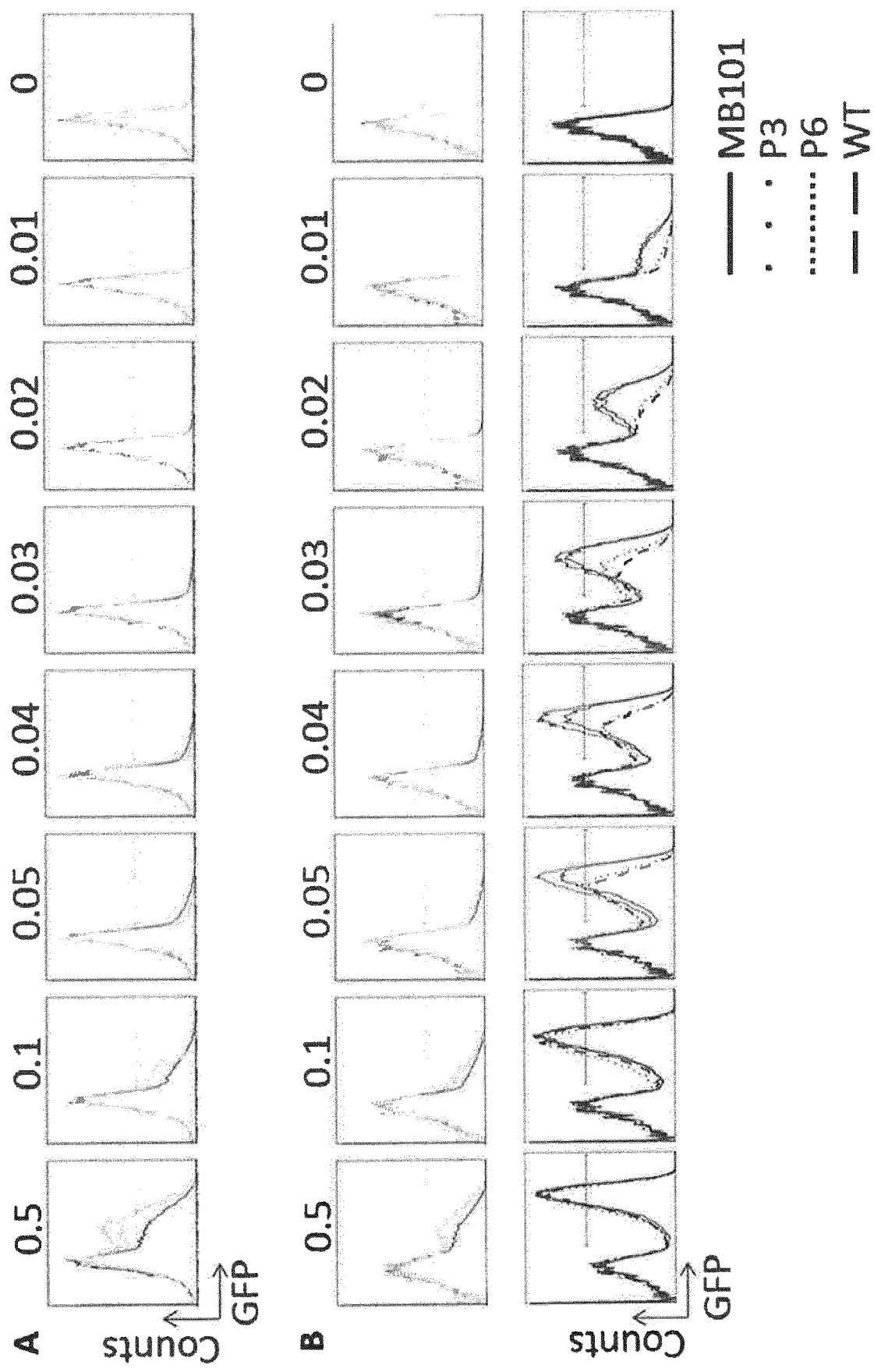
FIG. 12: MB101 (anti-CD303 $IgG_4$ S241P/R409K) and Pool 6 (anti-CD303 $IgG_4$ R409K) induce significantly more GFP expression in BDCA-2 transfectants than Pool 3 (anti-CD303 $IgG_4$ S241 P) or the wt $IgG_4$. To examine whether MB101, the wt $IgG_4$ and the two single mutation variants differ in their binding to BDCA-2, the induction of GFP expression was analyzed in transfectants constitutively expressing BDCA-2. (A) mAbs were added at the indicated concentrations to medium alone and then 1×10⁵ BDCA-2 transfectants were added. Percentage of GFP⁺ cells was analyzed after 24 h of culture by using an LSRII and FlowJo software. (B) Antibodies were added at the indicated concentrations to 1×10⁵ CD99 (upper row) or CD32b (lower row) transfectants before adding 1×10⁵ BDCA-2 transfectants. Percentage of GFP⁺ cells was analyzed after 24 h of culture. One typical experiment is shown.

As shown in FIG. 12A, addition of the soluble antibodies to the BDCA-2 transfectants resulted in GFP induction when high concentrations of MB101 were used, while the different antibody variants behaved overall similarly. When additionally the CD99 control transfectant was added BDCA-2 transfectants showed only background GFP expression, whereas co-culture with CD32b transfectants lead to massive GFP induction (FIG. 12B lower row). This expression varied between the antibody variants, especially when concentrations of 0.05 to 0.01 µg mAb were used. There one can see that MB101 (aCD303-hIgG$_4$-S241P/R409K) and Pool 6 (aCD303-hIgG$_4$-R409K) induce higher GFP levels than Pool 3 (aCD303-hIgG$_4$-S241P) or the wt antibody.

Figure 13:
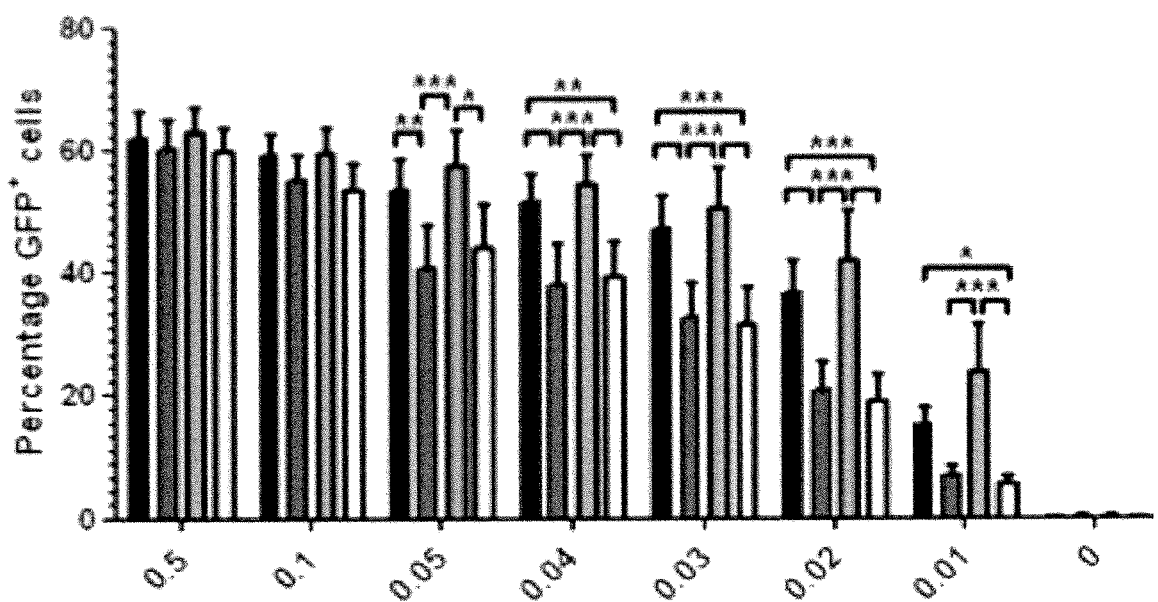
FIG. 13: Incubation of BDCA-2 transfectants with MB101 (anti-CD303 IgG$_4$ S241 P/R409K) and Pool 6 (anti-CD303 IgG$_4$ R409K) induce significantly more GFP expression than Pool 3 (anti-CD303 IgG$_4$ S241P) and the wt IgG$_4$. To examine whether MB101, the wt IgG$_4$ and the two single mutation variants differ in their binding to BDCA-2, GFP induction of BDCA-2 transfectants was analyzed. (A) Antibodies were added at the indicated concentrations to 1×10⁵ CD32b transfectants and then 1×10⁵ BDCA-2 transfectants were added. Percentage of GFP⁺ BDCA-2 transfectants was analyzed after 24 h of culture. Percentage of GFP⁺ cells was analyzed after 24 h of culture by using an LSRII and FlowJo software. (B) like (A) but the mean fluorescence intensity (MFI) was analyzed. Data from five independent experiments are shown. Statistical analysis was performed using a two-way Anova with Tukey's multiple comparison test.
Figure 13:
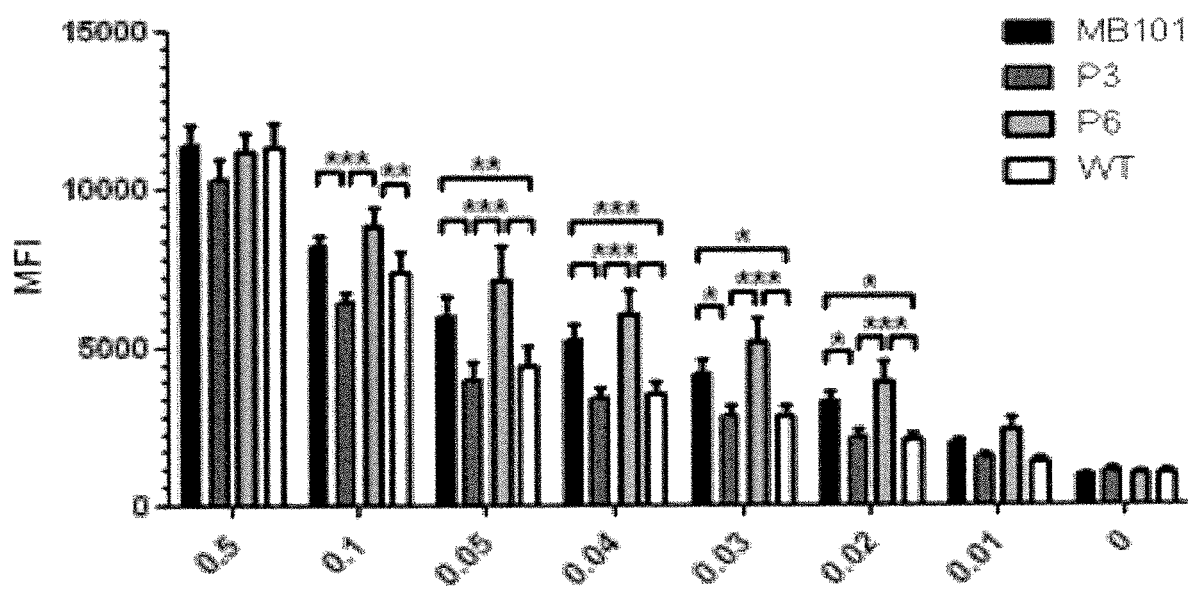

To verify this data and to perform statistical analysis, experiments were as shown in FIG. 13 repeated. Addition of the highest concentration of the antibodies (0.5 µg) in soluble form and without subsequent crosslinking to the BDCA-2 transfectants already sufficed to trigger GFP expression of the transfectants (data not shown). Nevertheless, the extent of GFP expression wanes with lower antibody concentrations markedly. In the co-culture experiments of the CD32b transfectants and the BDCA-2 transfectant incubated with the highest antibody concentrations no significant differences of GFP induction were detected. Nevertheless, there seems to be a trend that MB101 (aCD303-hIgG$_4$-S241P/R409K) and Pool 6 (aCD303-hIgG$_4$-R409K) induce slightly more GFP expression than the other antibodies. This trend gets significant starting at concentrations of 0.05 µg of antibody used. This phenomenon can be detected by analyzing the percentage of GFP$^+$ cells (FIG. 13A) as well as the mean fluorescence intensity (MFI) of the GFP signal (FIG. 13B). These results clearly indicate that introducing stabilizing mutation R409K into the hinge region of an IgG$_4$ antibody does not only change the FcγR binding profile of the antibody but may also enhances the specific antigen binding capacity by immobilizing the Ab via cell surface FcγR thereby providing functional advantage against WT IgG$_4$ variants.

Example 4— S241P and R409K Stabilize IgG$_4$

Formation of half-molecules and Fab arm exchange are inherent phenomena considering IgG$_4$. Mutations in the hinge region, i.e. S241P, and/or the CH3-domain, i.e. R409K, are analyzed in the present example for their capacity to eliminate dissociation of aCD303-IgG$_4$ antibodies into half-molecules and occurrence of Fab arm exchange intermediates.

Antibodies

| Specifity | Lot |
|---|---|
| aCD303-hIgG$_4$-WT | Miltenyi Biotec, |
| aCD303-hIgG$_4$-S241P | Miltenyi Biotec |
| aCD303-hIgG$_4$-R409K | Miltenyi Biotec |
| aCD303-hIgG$_4$-S241P/R409K | Miltenyi Biotec |
| Tysabri ® | CH080808.03 |
| Remicade ® | Klon: CA2, Charge: 5040102008 |
| AC144 (aCD303-mIgG$_1$) | Lot 008 |
| human IgG$_4$-λ | CH 091202.24 |
| Mouse anti-human-κ-HRP | Southern Biotech, Clone HP6062, Lot: D2703-5716B; CPD090429.01; FE100112.04 |

Buffers and Dilutions

| Buffer/dilution | composition |
|---|---|
| 10x PBS | 400.3 g sodium chloride<br>57.5 g disodium hydrogen phosphate<br>9.7 g potassium chloride<br>9.55 g potassium dihydrogen phosphate<br>ad 5000 mL with H$_2$O |
| 1x PBS | 100 mL 10xPBS<br>ad 1000 mL with H$_2$O |
| DTT 1M | 0.154 g DTT<br>ad 1 mL with H$_2$O |
| GSH 0.1M | 15.5 mg GSH<br>ad 1 mL with H2O |

Abbreviations

| | |
|---|---|
| ADCC | antibody-dependent cell-mediated cytotoxicity |
| BCA | bicinchoninic acid |
| BSA | bovine serum albumin |
| DMSO | dimethyl sulfoxide |
| DTT | dithiotreitol |
| EDTA | 2,2',2'',2'''-(ethane-1,2-diyldinitrilo)tetraacetic acid |
| ELISA | enzyme-linked immunosorbent assay |
| Fab | fragment antigen-binding |
| Fc | fragment crystallizable region |
| GSH | glutathione, reduced |
| H$_2$SO$_4$ | sulfuric acid |
| HRP | horseradish peroxidase |
| IgG | immunoglobulin G |
| MSH | mercaptoethanol |
| PBS | phosphate buffered saline |
| SDS-PAGE | sodium dodecyl sulfate polyacrylamide gel electrophoresis |
| TMB | 3,3',5,5'-tetramethylbenzidine |
| Tris-HCl | 2-Amino-2-hydroxymethyl-propane-1,3-diol buffered hydrochloric acid |

SDS-PAGE Analysis

First, samples were applied non-boiled and boiled on non-reducing gels. 3.5 µg aCD303-IgG$_4$-wt, 2.5 µg Tysabri®, 2.5 µg Remicade® and 2.5 µg AC144 were applied. From all other antibodies, 5 µg were put on each gel. Antibodies were loaded native or boiled for 5 minutes at 94° C. As control, aCD303-IgG$_4$-wt was incubated with β-mercaptoethanol to show the completely dissociated heavy and light chains. Samples were put on 4-12% Tris/Glycin-SDS-gel. Each gel was run at 30 mA, 5 W, 200 V, 1 h 15 min and stained Coomassie.

For non-boiled samples, all antibody bands could be seen around the 170 kDa marker band, corresponding to the whole antibody, which is approx. 150 kDa. aCD303-hIgG$_4$-R409K showed also a high molecular weight contaminating band. This could be due to cultivation of antibody-producing cells in serum-containing media.

After boiling of samples, all antibody bands run above the 170 kDA marker band. Half-molecule formation, characterized by the band between the 72 kDa and 95 kDa marker bands, could only be seen for Tysabri® and aCD303-IgG$_4$-wt, comprising an IgG$_4$-wild type hinge-region. Half-molecule formation was significantly decreased for all three IgG$_4$ variants (faint bands). AC144 and Remicade® showed no half-molecule band, representing a stable IgG$_1$-phenotype. The high molecular weight contaminating band of aCD303-hIgG$_4$-R409K could be detected again. In addition, a band slightly above the 55 kDa marker band could be detected. This was suspected to be a co-purified protein contamination from the serum-containing cell culture.

In a second set of experiments, the antibodies were incubated in the presence of 1 mM DTT. Antibodies were pre-incubated with 1 mM or 1 M DTT for 1 hour at 37° C. Samples were loaded on 4-12% Tris/Glycin-SDS-gel. Each gel was run at 30 mA, 5 W, 200 V, 1 h 15 min and stained Coomassie. 3.5 μg aCD303-IgG$_4$-wt, 2.5 μg Tysabri®, 2.5 μg Remicade® and 2.5 μg AC144 were applied. From all other antibodies, 5 μg were put on each gel. As a control, aCD303-IgG$_4$-wt was incubated with β-mercaptoethanol to show the completely dissociated heavy and light chains.

After the incubation of samples with 1 mM DTT, AC144 and Remicade® dissociated into H2 and light chains. In contrast, aCD303-IgG$_4$-wt and aCD303-hIgG$_4$-S241P dissociated completely into light and heavy chains. Tysabri® also showed a residual half-molecules band (upper band). IgG$_4$ variants R409K and S241 P/R409K showed the same pattern of H2 and light chain bands as the IgG$_1$ isotype antibodies AC144 and Remicade®, demonstrating the desired stabilized phenotype. These results demonstrated, that IgG$_1$ stability could be restored for the IgG$_4$ variants R409K and S241 P/R409K with mutation R409K having the most profound effect.

For all antibodies, DTT concentration was set to 1 M DTT. The pattern of bands was comparable to the treatment with 1 mM DTT for all antibodies except for Tysabri®. Tysabri® did not show any half-molecules but dissociated completely into heavy and light chains. Altogether, results for the reduction with 1 mM DTT were verified in 4 experiments; results for the reduction with 1 M DTT were verified in 2 experiments.

In a last experimental set-up, antibodies were incubated with 1 mM GSH, according to physiological GSH concentration (Michelet et al., 1995). Hereby, Tysabri® and aCD303-hIgG$_4$-wt dissociated into half-molecules, whereas all the other antibodies were stable. 3.5 μg aCD303-IgG$_4$-wt, 2.5 μg Tysabri®, 2.5 μg Remicade® and 2.5 μg AC144 were applied. From all other antibodies, 5 μg were put on each gel. Antibodies were put on pre-incubated with 1 mM GSH for 1 hour at 37° C. Samples were put on 4-12% Tris/Glycin-SDS-gel and gel was run at 30 mA, 5 W, 200 V, 1 h 15 min. afterwards, gel was stained Coomassie. As a control, aCD303-IgG$_4$-wt was incubated with β-mercaptoethanol to show the completely dissociated heavy and light chains.

This also showed, that stability of aCD303-hIgG$_4$-R409K and aCD303-hIgG$_4$-S241 P/R409K was comparable to IgG$_1$ antibodies AC144 and Remicade® under physiological conditions in vitro.

Fc-Fc-Interaction-Assay with Coated Antibodies

To detect, whether antibodies are engaged in Fab arm exchange, assays in ELISA-format are commonly used. Van der Neut Kolfschoten et al. (2007) established an assay, in which plates are coated with one antigen and bispecific antibodies, binding to two antigens, are detected using the other antigen. Rispens et al. (2009) coupled IgG$_1$ and IgG$_4$ to a solid phase and determined binding of either IgG$_1$ or IgG$_4$. Thereby, they found that Fc-Fc-interactions take place when CH3-domains of IgG$_4$ or IgG$_1$ coupled to a solid phase as well as IgG$_4$ in the fluid phase dissociated slightly before binding. Binding of IgG$_4$ to immobilized IgG$_4$ is interpreted as an intermediate state of fab arm exchange, which cannot succeed, because one IgG$_4$ partner is bound to a solid phase.

For the present example, for each ELISA-plate, 12 mL of coating solution was prepared by diluting an antibody, in general AC144 antibody, to a concentration of 5 μg/mL in 1×PBS. Microplates were coated with 100 μL/well of coating solution and sealed with sealing tape on top of microplate to prevent evaporation. Incubation was performed overnight at 4° C. Plates were washed three times with 350 μL/well washing buffer with 10 seconds soaking between washes. To block potential nonspecific binding, 200 μL/well assay buffer were added and sealed plates were incubated for 2 h at room temperature. Plates could be stored at 4° C. for up to one week with blocking solution when they were tightly sealed with sealing tape.

Antibodies were diluted to 100 ng/mL using assay buffer. If samples were reduced with DTT or GSH, aliquots were pipetted into microcentrifuge tubes and appropriate volumes of reducing stock solutions were added. Reduction was performed at 37° C. for 1 h either in the incubator or in a thermomixer. For the assay, 100 μL/well of sample were applied and sealed plates were incubated for 2 h at room temperature. In general, samples were put on as duplicates and assay buffer was used as blank. When incubation was finished, plates were washed again three times with 350 μL/well washing buffer. Mouse anti-human-K-HRP, diluted 1:1,000 to 1:2,000 in assay buffer, was applied and plates were incubated with 100 μL/well for 1 h at room temperature. Afterwards, plates were washed three times with 350 μL/well washing buffer. For detection, 100 μL/well TMB were used and color reaction was stopped after approx. 5 minutes with 100 μL/well 10 sulfuric acid, resulting in a color change from blue to yellow. Absorbance was measured at 450 nm in a microtiter plate reader.

To find out, whether the aCD303-IgG$_4$ variants could be engaged in Fc-Fc-interactions, ELISA-plates were coated with AC144, and antibodies were incubated with 1-20 mM DTT in 1 mM-steps. Remicade® was also incubated with DTT to include a stable hIgG$_1$-antibody as control. Staining for non-stabilized Tysabri® was the brightest with highest OD (450 nm) values, followed by humanized CD303-IgG$_4$-wt and IgG$_4$ variant S241 P, resulting from binding of applied antibodies to the Fc-parts of coated antibodies. IgG$_4$ variants R409K and S241 P/R409K showed lowest staining comparable to Remicade®, demonstrating the desired stabilized phenotype. Results were verified in three experiments.

In the next experimental set-up, human IgG$_4$-λ was coated on ELISA-plates. Again, antibodies were incubated with 1-10 mM DTT and triplicates were applied. Again, non-stabilized Tysabri® showed brightest staining, followed by humanized CD303-IgG$_4$-wt and IgG$_4$ variant S241 P. IgG$_4$ variants R409K and S241 P/R409K showed lowest staining comparable to Remicade® and AC144. OD (450 nm) of these four antibodies was not much higher than blank measurements. Assay buffer, consisting of PBS and BSA, was used as blank. These results demonstrated again, that IgG$_1$ stability could be restored for the IgG$_4$ variants R409K and S241 P/R409K with mutation R409K having the most profound effect. In two orthogonal assays, non-reducing SDS-PAGE analyses and Fc-Fc-interaction-assays, aCD303-IgG$_4$ variants R409K and S241 P/R409K exhibited the most stabilized phenotype comparable to the IgG$_1$ isotype antibodies AC144 and Remicade®.

Example 5—Phase I Clinical Trial of MB101

MB101 is a humanized anti-BDCA-2 (anti-CD303) monoclonal antibody derived from the murine antibody AC144 using a germ line-based humanization strategy of the variable regions of the light and heavy chain. MB101 is a humanized IgG$_4$ with substitutions 409K and 241 P. Binding of BDCA-2 receptor by MB101 suppresses induction of interferon (IFN)-alpha production in plasmacytoid dendritic cells (PDC). Production of IFN-alpha by PDCs is considered to be a major pathophysiological factor in autoimmune diseases and triggering of BDCA-2 is presumed to be a potential therapeutic strategy for blocking production of IFN-alpha in patients.

The production of IFN-alpha by PDCs seems to be the critical event in the induction of psoriatic inflammation and there is experimental evidence that inhibition of this process by ligation of the blood dendritic cell antigen (BDCA)-2 receptor on skin resident PDCs, using the murine predecessor monoclonal antibody AC144, may abrogate the development of psoriatic symptoms [Nestle et al. Plasmacytoid predendritic cells initiate psoriasis through interferon-a production. J Exp Med. 2005 Jul. 4; 202(1): 135-43]. Current monoclonal antibody therapies for patients with psoriasis are based on the neutralization of TNF-alpha, IL-12/IL-23 and IL-17, with an intention to interrupt the activation cycle by neutralizing central inflammatory cytokines. The MB101 approach is believed to influence an earlier phase of the inflammatory cycle and may therefore be an alternative approach to treat plaque psoriasis by preventing the induction of pro-inflammatory cytokines downstream of the IFN-alpha induction.

The mode of action of MB101 was investigated using the murine predecessor molecule monoclonal antibody (mAb) AC144 on human PDCs in vitro. Binding of BDCA-2 antigen by MB101 potently suppresses the induction of IFN-α/β production in human PDC, presumably by a mechanism dependent on calcium mobilization and protein-tyrosine phosphorylation by src-family protein-tyrosine kinases [Dzionek et al. BDCA-2, BDCA-3, and BDCA-4: three markers for distinct subsets of dendritic cells in human peripheral blood. J Immunol. 2000 Dec. 1; 165(11): 6037-46.; Dzionek et al. BDCA-2, a novel plasmacytoid dendritic cell-specific type II C-type lectin, mediates antigen capture and is a potent inhibitor of interferon alpha/beta induction. J Exp Med. 2001 Dec. 17; 194(12): 1823-34.; Dzionek et al. Plasmacytoid dendritic cells: from specific surface markers to specific cellular functions. Hum Immunol. 2002 December; 63(12):1133-48.].

Using mAb AC144, the induction of IFN-α/β production was significantly inhibited by the ligation of BDCA-2, even if the IFN-alpha inducing stimulus was added up to 6 days later and was independent from the stimulus used. This indicates that the ligation of BDCA-2 by mAb AC144 may induce a long-lasting inhibition of IFN-α/β production in PDC, i.e. that there is a difference between the pharmacokinetic and pharmacodynamic half-life of mAb AC144 and therefore MB101 in vivo.

In a recent phase I clinical study (M-2011-255), safety and tolerability of ascending single i.v. doses of MB101 in patients with psoriasis was assessed. Overall, single doses of MB101 in doses of 0.025 to 32.4 μg/kg body weight were safe and wen-tolerated. From dose levels 4.05 μg/kg to 32.4 μg/kg (groups 6 to 9), MB101 concentrations could be quantified in serum. Two subjects (one in dose group 6, one in dose group 8) treated with MB101 showed a strong increase in secretion levels of IFN-alpha at 24 h post dose. With the exception of these subjects, for the dose groups 7-9 a decrease in IFN-alpha production in samples from treated subjects could be observed. IFN-alpha levels at 24 h compared to baseline were lower in the subjects treated with MB101 than in those treated with placebo. In the last dose-group (group 9) the reduction of IFN-alpha production upon CpG-A stimulation was significant and showed up to approx. 80% decrease when compared to the pre-dose control sample from the same subject.

The decrease of MFI values of BDCA-2 staining on PBMCs showed clear dose-response, the effect being most pronounced at higher dose levels. After doses of 16.2 μg/kg and 32.4 μg/kg, Mean fluorescence intensity (MFI) values of BDCA-2 staining decreased to about 10% to 20% of the baseline value. The relationship of MFI values of BDCA-2 staining to the dose showed a sigmoidal course. MFI values of BDCA-2 staining on PBMCs decreased with increasing doses. Hence, there was a clear decrease of BDCA-2 staining on PBMCs with increase of dose. The foregoing data makes it plausible that MB101 can be suitably used for the treatment of an autoimmune disease such as psoriasis.

LIST OF REFERENCES

WO 2014/144542 A2
WO 2009/083009
Aalberse and Schuurman: IgG$_4$ breaking the rules. (Immunology 105 (2002); 9-19)
Bartholomaeus et al.: Cell contact-dependent priming and Fc interaction with CD32+ immune cells contribute to the TGN1412-triggered cytokine response. *J Immunol* 2014; 5: 2091-8.
Blank, et al.: Decreased transcription of the human FCGR2B gene mediated by the −343 G/C promoter polymorphism and association with systemic lupus erythematosus. *Hum Genet* 2005; 2-3: 220-7.
Blomberg et al.: Expression of the Markers BDCA-2 and BDCA-4 and Production of Interferon-alpha by Plasmacytoid Dendritic Cells in Sytsemic Lupus Erythematosus. *Arthritis & Rheumatism* 2003; 48(9): 2524-2532.
Bloom et al.: Intrachain disulfide bond in the core hinge region of human IgG$_4$. (Protein Science Vol 6 (1997); 407-415).
Chu et al. Inhibition of B cell receptor-mediated activation of primary human B cells by coengagement of CD19 and FcgammaRIIb with Fc-engineered antibodies. *Molecular Immunology* 45(15): 3926-3933 (2008)
Dzionek et al.: BDCA-2, BDCA-3, and BDCA-4: three markers for distinct subsets of dendritic cells in human peripheral blood. J Immunol. 2000 Dec. 1; 165(11): 6037-46.
Dzionek et al.: Plasmacytoid dendritic cells: from specific surface markers to specific cellular functions. Hum Immunol. 2002 December; 63(12):1133-48.
Dzionek et al.: BDCA-2, a novel plasmacytoid dendritic cell-specific type II C-type lectin, mediates antigen capture and is a potent inhibitor of interferon alpha/beta induction. J Exp Med. 2001 Dec. 17; 194(12): 1823-34.
Forrer et al.: Chip-based gel electrophoresis method for for the quantification of half-antibody species in IgG$_4$ and their by- and degradation products. (Anal. Biochem. 334(1) (2004):81-88).

Horton et al. Antibody-Mediated Coengagement of FcγRIIb and B Cell Receptor Complex Suppresses Humoral Immunity in Systemic Lupus Erythematosus. *J Immunol* 2011; 186: 4223-4233.

Labrijn et al.: Therapeutic IgG$_4$ antibodies engage in Fab-arm exchange with endogenous human IgG$_4$ in vivo. (Nat Biotechnol. 27(8) (2009):767-71).

Means et al.: Human lupus autoantibody-DNA complexes activate DCs through cooperation of CD32 and TLR9. *Journal of Clinical Investigation* 2005; 115: 407-417.

Michelet et al.: Blood and Plasma Glutathione Measured in Healthy Subjects by HPLC: Relation to Sex, Aging, Biological Variables, and Life Habits. (Clinical Chemistry Vol. 41, No. 10 (1995): 1509-17).

Mimoto et al.: Engineered antibody Fc variant with selectively enhanced FcγRIIb binding over both FcγRIIa$^{R131}$ and FcγRIIa$^{H131}$. *Protein Engineering, Design & Selection* 2013; 26(10): 589-598.

Nestle et al.: Plasmacytoid predendritic cells initiate psoriasis through interferon-a production. J Exp Med. 2005 Jul. 4; 202(1): 135-43.

Niewold, 2011. Interferon Alpha as a Primary Pathogenic Factor in Human Lupus. *Journal of Interferon & Cytokine Research* 31(12): 887-892.

Nimmerjahn, F. and J. V. Ravetch. 2008. Fcγ receptors as regulators of immune responses. *Nature Reviews Immunology* 1:34-47.

Rispens et al.: Human IgG$_4$ binds to IgG$_4$ and conformationally altered IgG$_1$ via Fc-Fc interactions. J Immunol. 2009; 182(7): 4275-4281.

Salfeld: Isotype selection in antibody engineering. (Nat. Biotechnol., Vol. 25 No. 12 (2007):1369-72).

Schuurman et al.: The inter-heavy chain disulfide bonds of IgG$_4$ are in equilibrium with intra-chain disulfide bonds. (Molecular Immunology 38(2001), 1-8)

Van der Neut Kolfschoten: Anti-inflammatory activity of human IgG$_4$ antibodies by dynamic Fab arm exchange. (Science. 317(5844) (2007):1554-7).

Veri et al.: Therapeutic control of B cell activation via recruitment of Fcgamma receptor IIb (CD32B) inhibitory function with a novel bispecific antibody scaffold. Arthritis Rheum. 2010; 62(7): 1933-1943.

Vidarsson et al.: IgG Subclasses and Allotypes: From Structure to Effector Functions. *Frontiers in Immunology*, Vol. 5 (2014).

Vogel et al.: 2015. Antibody induced CD4 down-modulation of T cells is site-specifically mediated by CD64(+) cells. *Sci Rep* 18308.

---

The invention claimed is:

1. A method of activating human CD32b/c on CD32b/c expressing cells in the treatment of an autoimmune disease in a human subject, comprising the step of administering to said human subject a polypeptide comprising at least one human $IgG_4$ with a lysine at position 409 (409K), using the EU index according to Kabat, wherein the $IgG_4$ recognizes an epitope of BDCA-2 (CD303) and is capable of binding to human CD32b/c with a statistically significant ($p=0.05$) higher binding affinity than a wild-type human $IgG_1$ having the amino acid sequence of SEQ ID NO: 10 and than a wild-type human $IgG_4$ having the amino acid sequence of SEQ ID NO: 1, when subjecting the polypeptide and the wild type antibodies to an ELISA assay with 1 hour incubation at room temperature in 1×PBS on ELISA plates precoated with recombinant CD32b,
wherein the polypeptide comprises the heavy chain CDRs 1-3 shown in SEQ ID NOs: 2-4 and light chain CDRs 1-3 shown in SEQ ID NOs: 5-7.

2. The method of claim 1, wherein the autoimmune disease is an inflammatory autoimmune disease.

3. The method of claim 1, wherein the autoimmune disease is further characterized by increased plasma levels of autoantibodies as compared to healthy subjects.

4. The method of claim 1, wherein the autoimmune disease is selected from the group consisting of systemic lupus erythematosus, psoriasis, multiple sclerosis, and rheumatoid arthritis.

5. The method of claim 1, wherein the autoimmune disease is systemic lupus erythematosus or psoriasis.

6. The method of claim 1, wherein the human $IgG_4$ further comprises a proline at position 241 (241P).

7. The method of claim 1, wherein the human $IgG_4$ has the amino acid sequence of SEQ ID NO: 1 ($hIgG_4$) with a lysine at the position corresponding to position 409 (409K) and a proline at the position corresponding to position 241 (241P), using the EU index according to Kabat.

8. The method of claim 1, wherein the human $IgG_4$ 409K shows an increased activation of human CD32b/c as compared to wild type human $IgG_4$.

9. The method of claim 1, wherein the human $IgG_4$ 409K shows an increased activation of human CD32b/c as compared to wild type human $IgG_1$.

10. The method of claim 1, wherein said polypeptide is not fused to a bioactive peptide amino acid sequence.

11. The method of claim 1, wherein the polypeptide is a monoclonal antibody.

12. The method of claim 11, wherein the monoclonal antibody does not recognize an epitope of human CD32b/c via its antigen binding region.

13. The method of claim 11, wherein the monoclonal antibody is a monospecific antibody.

14. The method of claim 11, wherein the antibody comprises the heavy chain CDRs 1-3 shown in SEQ ID Nos: 2-4 and light chain CDRs 1-3 shown in SEQ ID Nos: 5-7.

15. The method of claim 11, wherein the antibody comprises the variable heavy chain of SEQ ID NO: 8 and the variable light chain of SEQ ID NO: 9.

16. The method of claim 1, wherein the human subject shows a dysregulation of CD32b expression, as compared to healthy subjects.

17. The method of claim 1, wherein
the human subject has a CD32b 695T allele or a 2B.4 haplotype of the CD32b gene, or both; or
wherein the human subject has a CD32b 695C allele or a 2B.1 haplotype of the CD32b gene, or both.

18. A method of activating human CD32b/c on CD32b/c expressing cells in the treatment of allergy in a human subject, comprising the step of administering to said human subject a polypeptide comprising at least one human IgG$_4$ with a lysine at position 409 (409K), using the EU index according to Kabat, wherein the IgG$_4$ recognizes an epitope of BDCA-2 (CD303) and is capable of binding to human CD32b/c with a statistically significant (p=0.05) higher binding affinity than a wild-type human IgG$_1$ having the amino acid sequence of SEQ ID NO: 10 and than a wild-type human IgG$_4$ having the amino acid sequence of SEQ ID NO: 1, when subjecting the polypeptide and the wild type antibodies to an ELISA assay with 1 hour incubation at room temperature in 1×PBS on ELISA plates precoated with recombinant CD32b,
wherein the polypeptide comprises the heavy chain CDRs 1-3 shown in SEQ ID NOs: 2-4 and light chain CDRs 1-3 shown in SEQ ID NOs: 5-7.

19. The method of claim 18, wherein the human IgG$_4$ further comprises a proline at position 241 (241P).

20. The method of claim 18, wherein the human IgG$_4$ comprises the amino acid sequence of SEQ ID NO: 1 (hIgG$_4$) with a lysine at the position corresponding to position 409 (409K) and a proline at the position corresponding to position 241 (241P), using the EU index according to Kabat.

21. The method of claim 18, wherein said polypeptide is not fused to a bioactive peptide amino acid sequence.

22. The method of claim 18, wherein the polypeptide is a monoclonal antibody.

23. The method of claim 22, wherein the monoclonal antibody does not recognize an epitope of human CD32b/c via its antigen binding region.

24. The method of claim 22, wherein the monoclonal antibody is a monospecific antibody.

25. The method of claim 22, wherein the antibody comprises the heavy chain CDRs 1-3 shown in SEQ ID Nos: 2-4 and light chain CDRs 1-3 shown in SEQ ID Nos: 5-7.

26. The method of claim 22, wherein the antibody comprises the variable heavy chain of SEQ ID NO: 8 and the variable light chain of SEQ ID NO: 9.

\* \* \* \* \*

SEQUENCE LISTING

```
<160> NUMBER OF SEQ ID NOS: 10

<210> SEQ ID NO 1
<211> LENGTH: 327
<212> TYPE: PRT
<213> ORGANISM: Homo sapiens

<400> SEQUENCE: 1

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 2
<211> LENGTH: 13
<212> TYPE: PRT
<213> ORGANISM: Artificial
<220> FEATURE:
<223> OTHER INFORMATION: MB101 heavy chain CDR1

<400> SEQUENCE: 2

Ser Gly Phe Ser Leu Ser Thr Ser Gly Met Gly Val Gly
1               5                   10

<210> SEQ ID NO 3
<211> LENGTH: 16
<212> TYPE: PRT
<213> ORGANISM: Artificial
<220> FEATURE:
<223> OTHER INFORMATION: MB101 heavy chain CDR2

<400> SEQUENCE: 3

His Ile Trp Trp Glu Asp Asp Lys Tyr Tyr Asn Pro Ser Leu Lys Ser
1               5                   10                  15

<210> SEQ ID NO 4
<211> LENGTH: 11
<212> TYPE: PRT
<213> ORGANISM: Artificial
<220> FEATURE:
<223> OTHER INFORMATION: MB101 heavy chain CDR3

<400> SEQUENCE: 4

Thr Arg Asn Trp Asp Tyr Tyr Thr Met Asp Tyr
1               5                   10

<210> SEQ ID NO 5
<211> LENGTH: 11
<212> TYPE: PRT
<213> ORGANISM: Artificial
<220> FEATURE:
<223> OTHER INFORMATION: MB101 light chain CDR1

<400> SEQUENCE: 5

Arg Ala Ser Gln Glu Ile Ser Gly Tyr Leu Ser
1               5                   10

<210> SEQ ID NO 6
```

```
<211> LENGTH: 8
<212> TYPE: PRT
<213> ORGANISM: Artificial
<220> FEATURE:
<223> OTHER INFORMATION: MB101 light chain CDR2

<400> SEQUENCE: 6

Tyr Ala Ala Ser Thr Leu Asp Ser
1               5

<210> SEQ ID NO 7
<211> LENGTH: 9
<212> TYPE: PRT
<213> ORGANISM: Artificial
<220> FEATURE:
<223> OTHER INFORMATION: MB101 light chain CDR3

<400> SEQUENCE: 7

Leu Gln Tyr Ala Ser Tyr Pro Pro Thr
1               5

<210> SEQ ID NO 8
<211> LENGTH: 227
<212> TYPE: PRT
<213> ORGANISM: Artificial
<220> FEATURE:
<223> OTHER INFORMATION: MB101 heavy chain variable region

<400> SEQUENCE: 8

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Glu Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr Arg Asn Trp Asp Tyr Tyr Thr Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro
225
```

```
<210> SEQ ID NO 9
<211> LENGTH: 214
<212> TYPE: PRT
<213> ORGANISM: Artificial
<220> FEATURE:
<223> OTHER INFORMATION: MB101 light chain variable region

<400> SEQUENCE: 9

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Thr Asp Phe Thr Leu Thr Ile Ser Ser Leu Gln Ser
65                  70                  75                  80

Glu Asp Phe Ala Thr Tyr Tyr Cys Leu Gln Tyr Ala Ser Tyr Pro Pro
                85                  90                  95

Thr Phe Gly Gly Gly Thr Lys Leu Glu Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 329
<212> TYPE: PRT
<213> ORGANISM: Homo sapiens

<400> SEQUENCE: 10

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
```

-continued

```
            100                 105                 110
Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```